(12) United States Patent
Sauter et al.

(10) Patent No.: US 7,056,348 B2
(45) Date of Patent: *Jun. 6, 2006

(54) 5-ARYL-1,3,3-TRIMETHYL-2-METHYLENE-INDOLINE DERIVATIVES AND SALTS THEREOF, METHODS FOR THE PRODUCTION AND USE OF SAID COMPOUNDS FOR THE TEMPORARY COLORATION OF FIBERS

(75) Inventors: Guido Sauter, Thoerishaus (CH); Hans-Juergen Braun, Ueberstorf (CH); Nadia Reichlin, Cugy (CH)

(73) Assignee: Wella AG, Darmstadt (DE)

( * ) Notice: Subject to any disclaimer, the term of this patent is extended or adjusted under 35 U.S.C. 154(b) by 410 days.

This patent is subject to a terminal disclaimer.

(21) Appl. No.: 10/297,369

(22) PCT Filed: Jan. 24, 2002

(86) PCT No.: PCT/EP02/00706

§ 371 (c)(1),
(2), (4) Date: Dec. 4, 2002

(87) PCT Pub. No.: WO02/085854

PCT Pub. Date: Oct. 31, 2002

(65) Prior Publication Data

US 2003/0213071 A1   Nov. 20, 2003

(30) Foreign Application Priority Data

Apr. 19, 2001 (DE) ................................ 101 19 204

(51) Int. Cl.
*A61K 7/13* (2006.01)
(52) U.S. Cl. ...................... 8/405; 8/426; 8/587; 8/607; 8/608; 8/917; 8/918; 548/312.1
(58) Field of Classification Search .................. 8/405, 8/426, 917, 918, 587, 607, 608; 548/312.1
See application file for complete search history.

(56) References Cited

U.S. PATENT DOCUMENTS

| 3,865,837 A | 2/1975 | Krutak | .................. 260/326.11 |
| 5,246,989 A * | 9/1993 | Iwamoto et al. | ............... 524/89 |
| 6,652,601 B1 * | 11/2003 | Sauter et al. | .................. 8/405 |

FOREIGN PATENT DOCUMENTS

DE         1 949 716         4/1970

(Continued)

OTHER PUBLICATIONS

Tolmachev, A.A., et al: "5-Heteroaryl-Substituted . . . " Chem Heterocycl, Compd. (Engl Transl of Khim Geterotsiki Soedin.) 1991, 877-880.

(Continued)

*Primary Examiner*—Eisa Elhilo
(74) *Attorney, Agent, or Firm*—Michael J. Striker

(57) ABSTRACT

A method for the synthesis of 5-aryl-1,3,3,-trimethyl-2-methylene-indoline derivatives of Formula (I) or its salts of Formula (Ia)

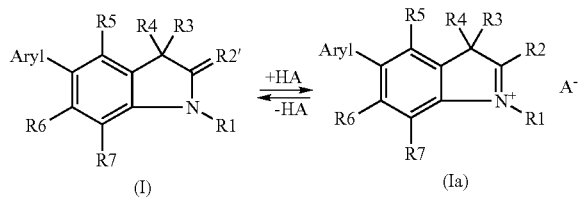

wherein 1 mole of a 5-aryl-2,3,3-trimethyl-3H-indole derivative of Formula (VII) is reacted for 1 to 44 hours at a temperature of 20° to 180° C. in an apolar, aprotic or polar, protic or polar aprotic solvent with 1 to 50 moles of a compound of Formula R1-A; new compounds of Formulas (I)/(Ia) and (V), obtainable by this method

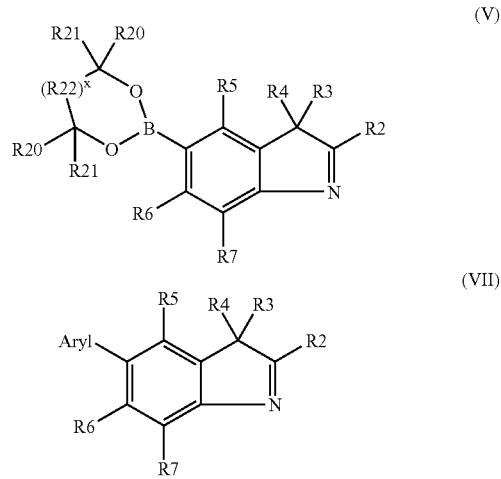

as well as an agent containing at least one compound of Formula (I)/(Ia) and a carbonyl/imine compound for dyeing keratinic fibers and a method for temporarily dyeing keratin fibers, for which the keratin fiber is dyed with the aforementioned agent and the dyeing, so obtained, is removed again at any later time by a sulfite preparation.

11 Claims, No Drawings

FOREIGN PATENT DOCUMENTS

| | | |
|---|---|---|
| DE | 22 02 300 A | 8/1973 |
| DE | 25 03 098 A | 7/1976 |
| EP | 0 449 669 A | 10/1991 |
| WO | 00 33799 A | 6/2000 |
| WO | 00 38639 A | 7/2000 |

OTHER PUBLICATIONS

Beretta, P., et al: "Correlations Between the Acid-Base Equilibriums and . . . " Photogr. Schi. Eng. (1974), 1892), pp. 197-207.

Patent Abstracts of Japan vol. 2000, No. 04, Aug. 31, 2000, & JP 2000 026469 A, Jan. 25, 2000.

Patent Abstracts of Japan vol. 1996, No. 05, May 31, 1996 & JP 08 027155 A, Jan. 30, 1996.

Database CA [On Line] Chemical Abstracts Service, Columbus, Ohio, US; Lazarenko, I. B. et al: "Synthesis and Photochromic Properties of . . . ". Retrieved from STN Database Accession No. 98:89141.

Gal'Bershtam, M, et al: "Synthesis and Spectral Characteristics . . . " Chem Heterocycl Compd. (Engl Transl of Khim. Geterotsiki Soedin.) 1976, 12, pp. 417-419.

Chemicabstract NR. 1976: 462913 Der Russischen Veroeffentlichung Khimiya Geterotsiklicheskikh Soedinenii 1976, pp. 497-499.

Dissertation of Andreas Leiminer, University Regensburg, 1995.

D.J. Gale et al: "Fibre-Reactive Basic Dyes . . . "In Soc. Dyers Color, 1974, pp. 97-100.

S.L. Buchwald et al: "Highly Active Palladium Catalysts . . . " In Journal of the American Chemical Society, 1999, 121, pp. 9550-9561.

S.L. Buchwald and J. M. Fox,: the Strem Chemiker: Recent Progress in the Suzuki Reactions of Aryl Chlorides, vol. XVII, May 1, 2000, pp. 1-33.

* cited by examiner

5-ARYL-1,3,3-TRIMETHYL-2-METHYLENE-INDOLINE DERIVATIVES AND SALTS THEREOF, METHODS FOR THE PRODUCTION AND USE OF SAID COMPOUNDS FOR THE TEMPORARY COLORATION OF FIBERS

BACKGROUND OF THE INVENTION

The object of the present invention is the use of 5-aryl-1,3,3-trimethyl-2-methylene-indoline derivatives as well as their physiologically tolerated salts with organic or inorganic acids as dye precursors in dyeing agents for fibers, especially of human hair, it being possible, if desired, to decolorize the dyeing obtained gently at a convenient later time. A further object of the invention are 5-aryl-1,3,3-trimethyl-2-methylene-indoline derivatives, as well as a method for their synthesis.

From the Chemical Abstract No. 1976:462913 of the Russian publication Khimiya Geterotsiklicheskikh Soedinenii 1976, pages 497–499, a method for the synthesis of 5-phenyl-1,3,3-trimethyl-2-methylene-indoline and 4-methoxyphenyl-1,3,3-trimethyl-2-methylene-indoline is known, which starts out from a corresponding arylhydrazine derivative. Since the corresponding arylhydrazine must first be synthesized for each aryl modification for this method the latter is rather expensive and unsuitable for the parallel synthesis of structurally related 5-aryl-1,3,3-trimethyl-2-methylene-indoline derivatives.

SUMMARY OF THE INVENTION

It was therefore an object to make available a method for synthesizing 5-aryl-1,3,3-trimethyl-2-methylene-indoline derivatives, which, starting out from a key building block, enables a large number of structurally related 5-aryl-1,3,3-trimethyl-2-methylene-indoline derivatives to be synthesized easily in good yield with a few reaction steps.

Surprisingly, and has now been found that, by an N-alkylation of 5-aryl-2,3,3-trimethyl-3H-indole derivatives of Formula (VII), the 5-aryl-1,3,3-trimethyl- 2-methylene-indoline derivatives of Formula (I) or their salts of Formula (Ia) can be synthesized easily, the compounds of Formula (VII) being obtained in good yield by a Suzuki reaction of an indole derivative of Formula (II) or Formula (V) with arylboric acid derivatives of Formula (III) or by a Suzuki reaction of an indole derivative of Formula (II) with a diboron compounds of Formula (IV) and an aryl halide.

The object of the present invention therefore is a method for the synthesis of 5-aryl-1,3,3-trimethyl-2-methylene-indoline derivatives of Formula (I) or their salts of Formula (Ia),

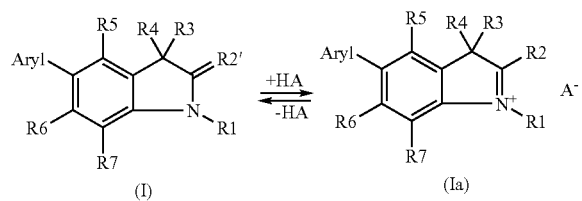

wherein 1 mole of a 5-aryl-2,3,3-trimethyl-3H-indole derivative of Formula (VII) is reacted for 1 to 44 hours at a temperature of 20° to 180° C. in an apolar, aprotic or polar, protic or polar, aprotic solvent with 1 to 50 moles of a compound of Formula R1-A

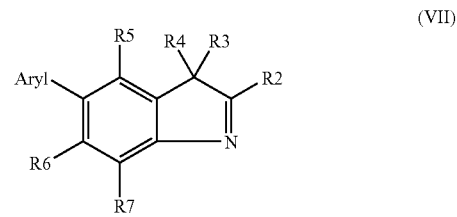

in which
R1 is a linear or branched C1–C8 alkyl group, a C1 to C8 monohydroxyalkyl group, a C2–C8 polyhydroxyalkyl group, a C1–C8 alkoxy-(C1–C8) alkyl group, a thio-(C1–C8)-alkyl group, a —(CH$^2$)$_m$—X—(CH$_2$)$_n$—Y—(CH$_2$)$_p$R$^a$ group, a —(CH$_2$)$_n$—X—R$^a$ group, a —(CH$^2$)$_m$—Y—(CH$_2$)$_n$—X—(CH$_2$)$_p$—R$^a$ group, a —(CH$^2$)$_m$—CO—(CH$_2$)$_p$—X—R$^a$ group, a —(CH$^2$)$_p$—R$^a$ group, a —(CH$_2$)$_m$—X—(CH$_2$)$_p$—CO—Y—R$^a$ group or one of the 3 following groups

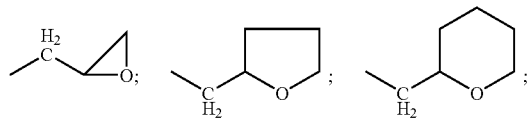

in which X and Y, independently of one another, are an oxygen atom, a sulfur atom or an NR$^b$ group, R$^a$ and R$^b$, independently of one another, are a hydrogen atom, an optionally substituted aromatic carbon ring or a heterocyclic ring or a linear or branched C1–C8 alkyl group,
m and n, independently of one another are a whole number from 1 to 6 and p is a whole number from 0 to 6,
R2 is a linear C1–C6 alkyl group,
R2' is a CH—R' group, in which R' is hydrogen or a C1–C5 alkyl group,
R3 and R4 independently of one another are a linear or branched C1–C4 alkyl group (especially a methyl group), a —(CH$_2$)$_n$—R$^c$ group, a —(CH$_2$)$_m$—CHR$^c$—X—(CH$^2$)$_n$—R$^c$ group, a —(CH$_2$)$_n$—CO—R$^c$ group, a —(CH$^2$)$_n$—CO—XR$^c$ group, a —(CH$_2$)$_n$—CN group, a —(CH$_2$)$_n$—CH═C(CH$_3$)$_2$ group, a —(CH$^2$)$_m$—X—CHR$^c$—(CH$_2$)$_n$—R$^c$ group or a —(CH$_2$)$_n$CH═CH group,
X being an oxygen atom, a sulfur atom or an NR$^b$ group, m and n, independently of one another, are a whole number from 1 to 6 and R$^c$ is a hydrogen atom, an optionally substituted aromatic carbocyclic ring or heterocyclic ring or a linear or branched C1–C6 alkyl group, with the proviso that the
R3 and R4 groups, linked over a (CH$_2$)$_n$ group (with n a whole number from 1 to 3), can form a spiro compound together with the 3H carbon atom,
R5, R6 and R7, independently of one another, are a hydrogen atom, a linear or branched C1–C4 alkyl group, a C1–C4 hydroxyalkyl group, a hydroxy group, a methoxy group, a benzyl group, a halogen atom, a nitro group, a nitroso group, a cyano group, a trifluoromethyl group, a —CHO group, a —COR$^d$ group, a —COOH group, a —CO$_2$R$^d$ group, an —OCOR$^d$ group, an —OCH$_2$aryl group, an —SO₂NH₂ group, an —NH₂ group, an —NH₃⁺ group, an —NHR$^d$ group, an —NH₂R$^{d+}$ group, an —N(R$_d$)₂ group, an —N(R$^d$)₃⁺ group, an —NHCOR$^d$ group, an —NHCOOR$^d$ group, a —CH₂NH₂ group, a —CH²NHR$^d$ group, a —CH₂N(R$^d$)₂ group, a —CO₂CF₃ group, a —PO(OR$^d$)₂ group, an —SO₂CHF₂ group, an —SO₂CF₃ group, an —SO₂R$^d$ group or an —SR$^d$ group, R$^d$ being a hydrogen atom, an optionally substituted aromatic carbocyclic or heterocyclic ring or a C1–C6 alkyl group, with the proviso that the adjacent R6 and R7 groups, jointly with the carbon atoms of the aromatic nucleus, can also form the aromatic ring of a 5- or 6-membered alicyclic or aromatic ring, which optionally may contain one or more sulfur, nitrogen and/or oxygen atoms, and aryl is a substituted pyrimidyl group, a cyclic group of Formula (IX) or a heterocyclic group of Formula (X) or (XI) or (XII)

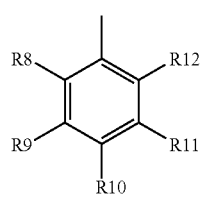

(IX)

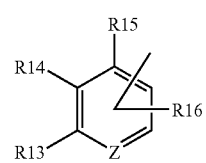

(X)

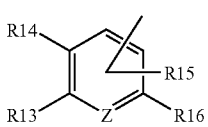

(XI)

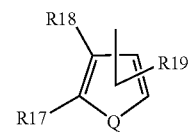

(XII)

in which R8, R9, R10, R11, R12, R13, R14, R15, R16, R17, R18 and R19 independently of one another are a hydrogen atom, a linear or branched C1–C4 alkyl group, a C1–C4 hydroxyalkyl group, a hydroxy group, a methoxy group, a benzyl group, a halogen atom, a nitro group, a nitroso group, a cyano group, a trifluoromethyl group, a —CHO group, a —COR$^e$ group, a —COOH group, a —CO₂R$^e$ group, an —OCOR$^e$ group, an —OCH₂aryl group, an —SO₂NH₂ group, an —NH₂ group, an —(NH₃)⁺ group, an —NHR$^e$ group, an —(NH₂R$^e$)⁺ group, an —N(R$^e$)₂ group, an —(N(R$^e$)₃)⁺ group, an —NHCOR$^e$ group, an —NHCOOR$^e$ group, a —CH₂NH₂ group, a —CH₂NHR$^e$ group, a —CH₂N(R$^e$)₂ group, a —CO₂CF₃ group, a —PO(OR$_e$)₂ group, an —SO₂CHF₂ group, an —SO₂CF₃ group, an —SO₂R$^e$ group or an —SR$^e$ group, with R$^e$ a hydrogen atom, an optionally substituted aromatic carbocyclic or heterocyclic ring or a C1–C6 alkyl group, with the proviso that two adjacent R8 to R19 groups, jointly with the carbon atoms of the aromatic nucleus, can also form a 5- or 6-membered alicyclic or aromatic ring, which optionally may contain one or more sulfur, nitrogen and/or oxygen atoms, and Z is sulfur, nitrogen, oxygen or an N$^{(+)}$—R$^f$ group, Q is sulfur, nitrogen, oxygen or an N—R$^f$ group, R$^f$ is hydrogen, a C₁–C₆ alkyl group, a C2–C4 hydroxyalkyl group, a phenyl group, an acetyl group or sulfonyl group, A⁻ is an anion of an organic or inorganic acid, preferably chloride, bromide, iodide, hydrogen sulfate, sulfate, toluenesulfonate, benzenesulfonate, monomethyl sulfate, hexafluorophosphate, perchlorate, hexafluoroantimonate, tetrafluoroborate, tetraphenylborate, formate, acetate or propionate, the chloride ion, the tetrafluoroborate ion, the acetate ion and the hydrogen sulfate ion being particularly preferred.

The compounds of Formula (VII) are N-alkylated preferably at a temperature of 40° to 120° C., a reaction temperature of 40° to 85° C. being particularly preferred. The reaction is carried out preferably for 4 to 24 hours and particularly for 4 to 8 hours in an apolar, aprotic or polar, protic solvent, such as, for example, benzene, toluene, alcohols such as methanol or ethanol, halogenated hydrocarbons such as chloroform or dichloromethane, acetonitrile and 3-methoxypropionitrile, benzene, toluene, methanol, ethanol, dichloromethane and chloroform being particularly preferred.

The compounds of Formula (VII) and the compound of Formula R1-A preferably are used in a molar ratio of 1:1.1 to 1:10 and particularly in a molar ratio of 1:1.1 to 1:2. The aforementioned reaction optionally can be carried at with the help of ultrasound or in an autoclave or a bomb tube under a positive pressure (0.1 to 50 bar, preferably 1 to 20 bar and particularly of 1 to 5 bar).

The 5-aryl-2,3,3-trimethyl-3H-indole derivatives of Formula (VII) can be synthesized easily by a Suzuki reaction either by the reaction of a 5-halogeno-2,3,3-trimethyl-3H-indole derivative of Formula (II) with an arylboric acid derivative of Formula (III) or by reaction of a 5-halogeno-2,3,3-trimethyl-3H-indole derivatives of Formula (II) with a diboron compound of Formula (IV) and an arylhalogen compound of Formula (VI).

The Suzuki reaction is carried out at 20° to 180° C., preferably at 40° to 120° C. and particularly at 60° to 100° C., in an apolar, aprotic solvent or a polar, protic solvent, such as nitriles, ether compounds or aromatic hydrocarbons, preferably benzene, toluene, tetrahydrofuran, dioxane, 1,2-dimethoxyethane, acetonitrile and 3-methoxypropionitrile, particularly toluene, tetrahydrofuran and 1,2-dimethoxyethane, with or without the addition of water, with the addition of a suitable catalyst (such as a palladium catalyst in an amount of 0.001 to 0.5 moles and particularly of 0.05 to 0.12 moles per mole of educt) and/or a suitable organic or inorganic base, such as, for example, sodium hydroxide, potassium hydroxide, potassium carbonate and potassium acetate, potassium carbonate and potassium acetate being particularly preferred. The reaction medium is free of oxygen, the reaction preferably being carried out under an inert gas such as argon or nitrogen. The duration of the reaction is about 1 to 24 hours, a reaction time of 1 to 8 hours and, especially, of 2 to 6 hours being preferred.

The method of synthesizing the compounds of Formulas (I)/(Ia), including the synthesis of the starting compounds of Formula (VII) is summarized in the following Diagram 1. In the following Diagram 1, the R1 to R7, aryl and A groups have been meaning given above, while R20 and R21, independently of one another, are a hydrogen atom or a linear or branched C1–C4 alkyl group, R22 is a linear or branched C1–C4 alkyl group, x is 0 or 1 and Hal represents an iodine, bromine or chlorine atom, a $CF_3$—$SO_2$—O group, the bromine atom and the chlorine atom being preferred, and R23 and R'23, independently of one another, represent hydrogen or a C1–C6 alkyl group, or R23 and R'23, together with the —O—B—O group, form a ring of Formula (VIII).

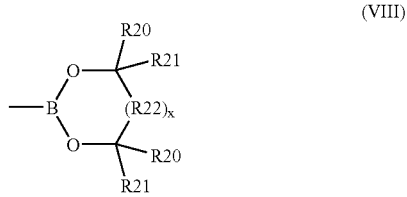

(VIII)

for example, with the help of the standard synthesis methods, known from the literature, as described, for example, in the dissertation of Andreas Leiminer, University of Regensburg (1995), the German Offenlegungsschrift 1949 716 or the U.S. Pat. No. 3,865,837. Moreover, further substituents, such as a nitro function, can be introduced at the aromatic ring by electrophilic substitution reactions known from the literature. In this connection, reference is made particularly to the synthesis method described by D. J. Gale, J. F. K. Wilshire in J. Soc. Dyers Colour: 1974, pages 97–100. By a subsequent treatment with reducing agents or oxidizing agents or with the help of suitable reactions, in which protective groups are added or eliminated, the introduced substituents optionally can be defunctionalized, as a result of which further compounds of the general Formula (II) can be obtained.

The Suzuki reaction can be carried out similarly to methods known from the literature, such as the methods, described by S. L. Buchwald et al. in the "Journal of the American Chemical Society", 121, 1999, pages 9550–9561.

Diagram 1

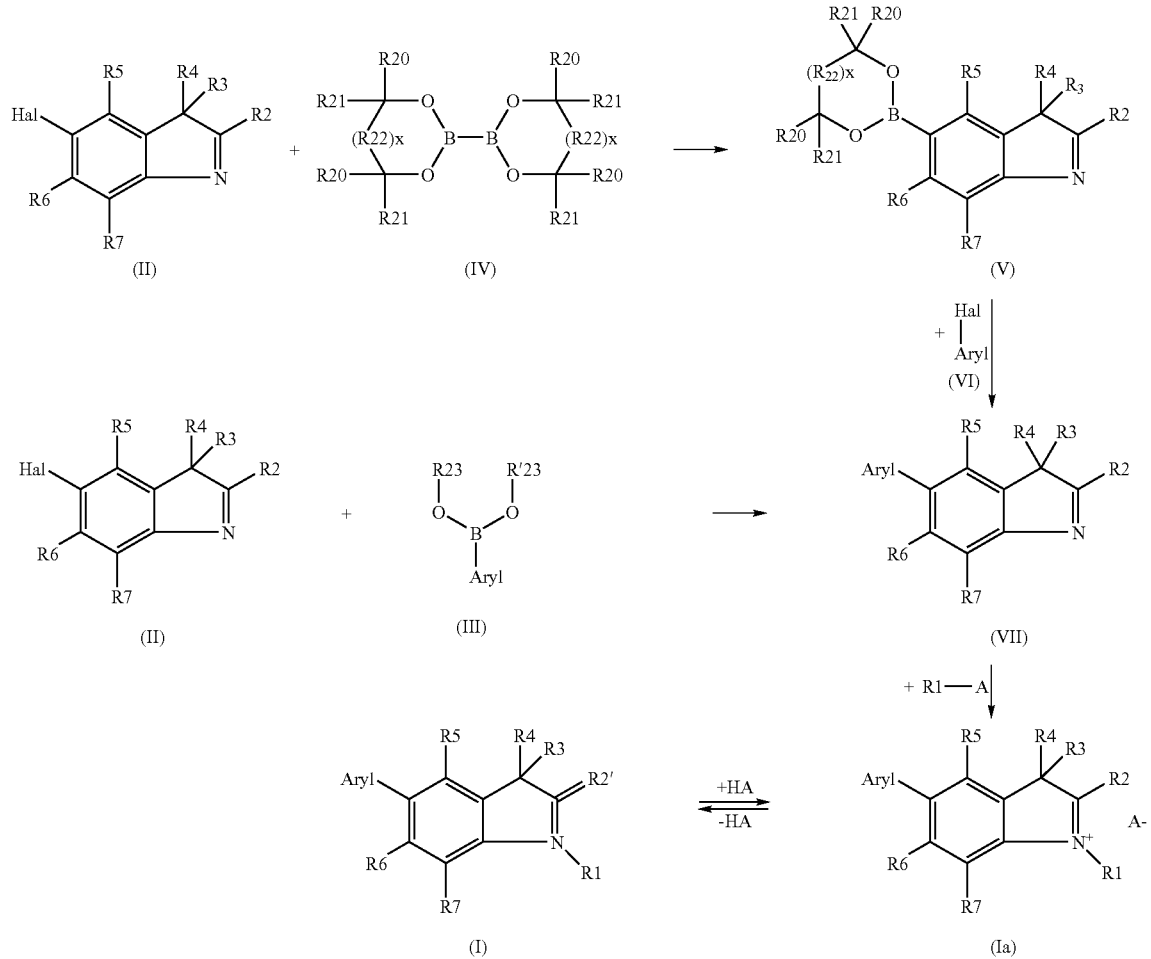

The starting compounds of Formulas (II), (III), (IV) and (VI) are known from the literature. The compounds of formulas (III), (IV) and (VI) can also be obtained commercially. The compounds of Formula (II) can be synthesized, In this connection, reference is also made to "The Strem Chemiker: Recent Progress in the Suzuki Reactions of Aryl Chlorides" of S. L. Buchwald and J. M. Fox, vol. XVIII, No. 1, May 2000, pages 1–33 and to the references cited there.

Compounds of Formulas (I) and (Ia) are also outstandingly suitable as dye precursors in non-oxidative systems for dyeing keratin fibers.

A further object of the present invention therefore is an agent for dyeing keratin fibers, such as wool, silk or hair, especially human hair, wherein (a) at least one compound of Formulas (I) and/or (Ia) and (b) at least one carbonyl compound and/or an imine compound is contained.

Although the compounds of Formula (I) and (Ia) are suitable particularly for being used to dye keratin fibers, it is, in principle, also possible to dye other natural or synthetic fibers, such as cotton or nylon 66 with these compounds.

As suitable compounds of Formulas (I) and (Ia), in particular, the following compounds as well as their salts may be mentioned: 5-(2,4-dimethoxyphenyl)-1,3,3-trimethyl-2-methylene-indoline, 5-(1,3-benzodioxol-5-yl)-1,3,3-trimethyl-2-methylene-indoline, 5-(2-(trifluoromethyl)phenyl)-1,3,3-trimethyl-2-methylene-indoline, 5-(phenyl)-1,3,3-trimethyl-2-methylene-indoline, 5-(p-tolyl)-1,3,3-trimethyl-2-methylene-indoline, 5-(naphthalene-1-yl)-1,3,3-trimethyl-2-methylene-indoline, 5-(4-methylsulfanyl-phenyl)-1,3,3-trimethyl-2-methylene-inodoline, 5-(4-hydroxyphenyl)-1,3,3-trimethyl-2-methylene-indoline, 5-(naphthalene- 2-yl)-1,3,3-trimethyl-2-methylene-indoline, 5-(2-hydroxy-naphthalene-6-yl)-1,3,3-trimethyl-2-methylene-indoline, 5-(anthracene-9-yl)-1,3,3-trimethyl-2-methylene-indoline, 5-(3,5-dimethyl-phenyl)-1,3,3-trimethyl-2-methylene-indoline, 5-(acenaphthene-5-yl)-1,3,3-trimethyl-2-methylene-indoline, 5-(4-methoxy-2-methyl-phenyl)-1,3,3-trimethyl-2-methylene-indoline, 5-(biphenyl-4-yl)-1,3,3-trimethyl-2-methylene-indoline, 5-(benzo[b]thiophene-3-yl)-1-ethyl-,3,3-dimethyl-2-methylene-indoline, 1-ethyl-3-(1-ethyl-3,3-dimethyl-2-methylene-2,3-dihydro-1H-indole-5-yl)pyridinium tetrafluoroborate, 5-(furan-3-yl)-1-ethyl-3,3-dimethyl-2-methylene-indoline, 5-(thiophene-3-yl)-1,3,3-trimethyl-2-methylene-indoline, 5-(thiophene-2-yl)-1-ethyl-3,3-dimethyl-2-methylene-indoline and 1-(1',3',3'-trimethyl-2'-methylene-2,3,2',3'-tetrahydro-1'H-[5,5']biindolyl-1-yl)-ethanone; the 5-(2,4-dimethoxyphenyl)-1,2,3,3-tetramethyl-3H-indole-1-ium-tetrafluoroborate, 5-(1,3-benzodioxol-5-yl)-1,2,3,3-tetramethyl-3H-indole-1-ium-tetrafluoroborate, 1,2,3,3-tetramethyl-5-(-2-trifluoromethyl)phenyl)-3H-indole-1-ium-tetrafluoroborate, 1,2,3,3-tetramethyl-5-(thiophene-3-yl)-3H-indolium-iodide, 5-phenyl-1,2,2,3-tetramethyl-1(3H)-indolium-tetrafluoroborate, 1,2,3,3-tetramethyl-5-p-tolyl-3H-indolium-tetrafluoroborate, 1,2,3,3-tetramethyl-5-naphthalene-1-yl-3H-indoilium-tetrafluoroborate, 1-ethyl-2,3,3-trimethyl-5-(4-methylfulfanyl-phenyl)-3H-indolium-tetrafluoroborate, 1-ethyl-5-(4-hydroxy-phenyl)-2,3,3-trimethyl-3H-indolium-tetrafluoroborate, 1-ethyl-2,3,3-trimethyl-5-naphthalene-2-yl-3H-indolium-tetrafluoroborate, 1-ethyl-5-(6-hydroxy-naphthalene-2-yl)-2,3,3-trimethyl-3H-indolium-tetrafluoroborate, 5-anthracene-9-yl-1-ethyl-2,3,3-trimethyl-3H-indolium-tetrafluoroborate, 5-(3,5-dimethyl-phenyl)-1-ethyl-2,3,3-trimethyl-3H-indolium-tetrafluoroborate, 5-benzo[b]thiophene-3-yl-1-ethyl-2,3,3-trimethyl-3H-indolium-tetrafluoroborate, 5-acenaphthene-5-yl-1-ethyl-2,3,3-trimethyl-3H-indolium-tetrafluoroborate, 1-ethyl-5-(4-methoxy-2-methyl-phenyl)-2,3,3-trimethyl-3H-indolium-tetrafluoroborate, 5-biphenyl-4-yl-1-ethyl-2,3,3-trimethyl-3H-indolium-tetrafluoroborate, 5-benzo[b]thiophene-3-yl-1-ethyl-2,3,3-trimethyl-3H-indolium-tetrafluoroborate, 1-ethyl-5-(1-ethyl-3-pyridiniumyl)-2,3,3-trimethyl-3H-indolin ditetrafluoroborate, 1-ethyl-5-furan-3-yl-2,3,3-trimethyl-3H-indolium-tetrafluoroborate, 1-ethyl-2,3,3-trimethyl-5-(2-thienyl)-3H-indolium tetrafluoroborate and 1'-acetyl-1-ethyl-2,3,3-trimethyl-2',3'-dihydro-3H, 1'H-[5,5']biindolyl-1-ium-tetrafluoroborate being particularly preferred.

As suitable carbonyl compound and imine compounds, the following, in particular, may be mentioned: 4-hydroxy-3-methoxy-benzaldehyde (vanillin), 3-hydroxy-4-methoxy-benzaldehyde (isovanillin), 3,4-dihydroxy-benzaldehyde, 4-hydroxybenzaldehyde, 3,5-dimethoxy-4-hydroxy-benzaldehyde, 4-dimethylaminobenzaldehyde, 4-methyl-5-imidazole-carboxaldehyde, 4-dimethylamino-cinnamon-aldehyde, 4-hydroxy-2-methoxy-benzaldehyde, 3,5-dimethyl-4-hydroxybenzaldehyde, 4-dimethylamino-2-methoxybenzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxy-biphenyl-1-carbaldehyde, 2-hydroxy-3-methoxybenzaldehyde, 2,4-dihydroxybenzaldehyde, 3,4-dihydroxy-benzaldehyde, 2,5-dihydroxy-benzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxy-benzaldehyde, 2,5-dimethoxy-benzaldehyde, 3,5-dimethoxybenzaldehyde, 3,4-dimethoxybenzaldehyde, indole-3-carbaldehyde, benzene-1,4-dicarbaldehyde, 4-ethoxybenzaldehyde, 2-methyl-1,4-naphthoquinone, 4-carboxy-benzaldehyde, 4-hydroxy-3-methoxy-cinnamon-aldehyde, 3,5-dimethoxy-4-hydroxy-cinnamon-aldehyde, 3-methoxy-4-(1-pyrrolidinyl)-benzaldehyde, 4-diethylamino-3-methoxybenzaldehyde, 1,2-phthaldialdehyde, pyrrole-2-aldehyde, thiophene-2-aldehyde, thiophene-3-aldehyde, chromone-3-carboxaldehyde, 6-methyl-4-oxo-1(4H)-benzopyran-3-carbaldehyde, N-methylpyrrol-2-aldehyde, 5-methyl-furfural, 6-hydroxy-chromene-3-carboxaldehyde, 6-methylindole-3-carboxaldehyde, 4-dibutylamino-benzaldehyde, N-ethylcarbazole-3-aldehyde, 4-diethylamino-2-hydroxybenzaldehyde, 3,4-dimethoxy-5-hydroxy-benzaldehyde, 5-(4-(diethylamino)phenyl)-2,4-pentadienal, 2,3-thiophene-dicarboxaldehyde, 2,5-thiophenedicarboxaldehyde, 2-methoxy-1-naphthaldehyde, 3-ethoxy-4-hydroxybenzaldehyde, 2-nitrobenzaldehyde, 3-nitro-benzaldehyde and 4-nitrobenzaldehyde, 4-(((2-hydroxyethyl)imino)methyl)-2-methoxyphenol, 5-(((2-hydroxyethyl)imino)methyl)- 2-methoxyphenol, 2,6-dimethoxy-4-(((2-hydroxyethyl)imino)methyl)phenol, 4-(((2-hydroxy-ethyl)imino)methyl)phenol, 1,2-dihydroxy-4-(((2-hydroxyethyl)imino)methyl)benzene, N,N-dimethyl-4-(((2-hydroxyethyl)imino)methyl)-aniline, 1,2-dihydroxy-3-(((2-hydroxyethyl)imino)methyl)benzene, 4-(((3-hydroxy-propyl)imino)methyl)phenol, 2,6-dimethoxy-4-(((3-hydroxypropyl)imino)methyl)phenol, 4-(((2,3-dihydroxypropyl)imino)methyl)phenol, 2,6-dimethoxy-4-(((2,3-dihydroxypropyl)imino)methyl)phenol, 2-[(4-hydroxy-benzylidene)-amino]-propane-1,3-diol, 2-[(4-hydroxy-3,5-dimethoxy-benzylidene)-amino]-propane-1,3-diol, 4-(((2-hydroxy-2-phenyl-ethyl)imino)methyl)phenol, 2,6-dimethoxy-4-(((1-phenyl-2-hydroxyethyl)imino)methyl)phenol, 4-(((2-hydroxyphenyl)imino)methyl)phenol, 2,6-dimethoxy-4-(((2-hydroxyphenyl)imino)methyl)phenol, 5-guanidino-2-[(4-hydroxy-benzylidene)-amino]-pentanoic acid, 2-[(4-dimethylamino-naphthalene-1-ylmethylene)-amino]-ethanol, 5-guanidino-2-[(4-hydroxy-3,5-dimethoxy-benzylidene)-amino]-pentanoic acid, 2-[(4-hydroxy-3,5-dimethoxy-benzylidene)-amino]-3-(3H-imidazole-4-yl)-propionic acid, 2-[(4-hydroxy-benzylidene)-amino]-3-(3H-imidazole-4-yl)-propionic acid, 2-[(4-hydroxy-3,5-dimethoxy-benzylidene)-amino]-3-(1H-indole-3-yl)-propionic acid, 2-[(4-hydroxy-benzylidene)-amino]-3-(1H-indole-3-yl)-propionic acid, 2-(((2-hydroxyethyl)imino)

methyl)phenol, 1,2-dihydroxy-3-(((2-hydroxyethyl)imino) methyl)benzene, 1,2,3-trihydroxy-4-(((2-hydroxyethyl) imino)methyl)benzene, 1,2,3,4-tetrahydroxy-5-(((2-hydroxyethyl)imino)methyl)benzene and 1,2,4-trihydroxy-4-(((2-hydroxyethyl)imino)methyl)benzene.

The carbonyl compounds may also be synthesized in situ by and Symantec oxidation of appropriate aryl alcohols and benzyl alcohols with the help of one or more suitable oxidation enzyme.

As suitable aryl alcohols and benzyl alcohols, the following compounds, in particular, a mentioned: benzyl alcohol, 4-hydroxy-benzyl alcohol, 4-hydroxy- 3-methoxy benzyl alcohol (vanillyl alcohol), 3-hydroxy-4-methoxy-benzyl alcohol (isovanillyl alcohol), 3,5-dimethoxy-4-hydroxy-benzyl alcohol, 3,4-dihydroxy-benzyl alcohol, 2-hydroxy-3-methoxy-benzyl alcohol, 4-ethoxy-benzyl alcohol, 4-carboxy benzyl alcohol, 2,5-dihydroxy-benzyl alcohol, 2,4-dihydroxy-benzyl alcohol, 2-hydroxy-benzyl alcohol, 3,5-dimethoxy-4-hydroxy-benzyl alcohol, 4-hydroxy-2-methoxy-benzyl alcohol, 2,4-dimethoxy-benzyl alcohol, 2,3-dimethoxy-benzyl alcohol, 2,5-dimethoxy-benzyl alcohol, 3,5-dimethoxy-benzyl alcohol, 3,4-methylenedioxy-benzyl alcohol, 3,4-dimethoxy-benzyl alcohol, 3-ethoxy-4-hydroxy-benzyl alcohol, 3,5-dimethyl-4-hydroxy-benzyl alcohol, 3,4-dimethoxy-5-hydroxy-benzyl alcohol, 3,4,5-trimethoxy-benzyl alcohol, 2,4,6-trihydroxy-benzyl alcohol, 3,4,5-trihydroxy-benzyl alcohol, 2,3,4-trihydroxy-benzyl alcohol, 3,5-di-t-butyl-4-hydroxy-benzyl alcohol, 2-nitro-benzyl alcohol, 3-nitro-benzyl alcohol, 4-nitro-benzyl alcohol, 2-amino-benzyl alcohol, 3-amino-benzyl alcohol, 3-amino-4-methyl-benzyl alcohol, 3,5-diamino-benzyl alcohol, 4-amino-benzyl alcohol, 4-dimethylamino-benzyl alcohol, 4-diethylamino-2-hydroxy-benzyl alcohol, 4-diethylamino-3-methoxy-benzyl alcohol, 4-dimethylamino-2-methoxy-benzyl alcohol, 4-dibutyl-amino-benzyl alcohol, 3-methoxy-4-(1-pyrrolidinyl)-benzyl alcohol, (4-methoxy-naphthalene-1-yl)-methanol, (4-dimethylamino-naphthalene-1-yl)-methanol, 2-(hydroxymethyl)-1-naphthol, 1-naphthalene-methanol, 2-naphthalene-methanol, (2-methoxy-naphthalene-1-yl)-methanol, 4-hydroxy-methyl-naphthalene-1-ol, 4'-hydroxymethyl-biphenyl-4-ol, (4-hydroxymethyl-phenyl)-methanol, 4-(3-hydroxy-propenyl)-2-methoxy-phenol, 4-(3-hydroxy-propenyl)-2,6-dimethoxy-phenol, 3-(4-dimethylamino-phenyl)-prop-2-ene-1-ol, 5-(4-(diethylamino-phenyl)-penta-2,4-diene-1-ol, thiophene-2-yl-methanol, (5-hydroxymethyl-thiophene-2-yl)-methanol, thiophene-3-yl-methanol, (1H-pyrrole-2-yl)-methanol, (1-methyl-1H-pyrrole-2-yl)-methanol, 5-methyl-furan-2-yl)-methanol, (1H-indole-3-yl)-methanol and (6-methyl-1H-indole-3-yl)-methanol.

As "oxidation enzyme," basically any enzyme can be used, which is able to catalyze the oxidation of the alcohol to an aldehyde or ketone. The following enzymes are mentioned as examples of these without limiting them to the ones mentioned: alcohol dehydrogenases (E.C. Classification 1.1.1-), alcohol oxidases (E.C. Classification 1.1.2- and 1.1.3.- and 1.1.99.-), flavin oxidases (E.C. Classification 1.2-), laccases (E.C. Classification 1.4.-), peroxidases (E.C. Classification 1.11.1.-), hydroxylases and monooxygenases (E.C. Classification 1.13.12- and 1.13.99.-), optimized enzymes, such as genetically modified enzymes, being particularly preferred for the oxidation of the alcohols used.

The enzyme is used preferably in an amount of 5–100 units per mmole of substrate (alcohol), one unit of enzyme activity being the amount of enzyme, which is required for the catalysis of the oxidation of 1 micromole of an alcohol per minute.

The compounds of Formulas (I) and/or (Ia) are kept separately from the carbonyl and imine compounds until shortly before use. The inventive dyeing agent therefore usually consists of two compounds, namely a dye carrier composition (A1), which contains the compounds of Formulas (I) and/or (Ia) and optionally substantive dyes, and a further dye carrier composition (A2), which contains the carbonyl/imine compounds and optionally substantive dyes. These two components are mixed directly before use to form a ready-for-use dyeing agent and are then applied on the fibers to be dyed. Of course, it is also possible for one or both components to consist of several individual components, which are mixed together before use. However, a 2-component kit, consisting of an agent of component (A1) and an agent of component (A2), is particularly preferred.

The compounds of Formulas (I) and/or (Ia) and the carbonyl/imine compound are contained in the respective dye carrier composition (component (A1) or component (A2), in each case in a total amount of about 0.02 to 20 percent by weight and preferably of 0.2 to 10 percent by weight, the compounds of Formulas (I) and/or (Ia) and the carbonyl/imine compound being contained in each case in a total amount of about 0.01 to 10 percent by weight and preferably of 0.1 to 5 percent by weight in the ready-for-use dyeing agents obtained by mixing components (A1) and (A2).

Moreover, the inventive dyeing agents may optionally contain additionally conventional, physiologically safe, substantive dyes from the group of acidic or basic dyes, nitro dyes, azo dies, quinone dyes and triphenylmethane dyes.

The substantive dyes may be used in component (A1) and/or component (A2) in each case in a total amount of about 0.02 to 20 percent by weight and preferably of 0.2 to 10 percent by weight, the total amount of substantive dyes in the ready-for-use dyeing agent, obtained by mixing components (A1) and (A2), being about 0.01 to 10 percent by weight and preferably 0.1 to 5 percent by weight.

The ready-for-use dyeing agent as well as the components (A1) and (A2) may be prepared, for example, in the form of a solution, especially an aqueous or aqueous-alcoholic solution. Further suitable forms of preparations are a cream, a gel, a foam or an emulsion. Their composition represents a mixture of the compounds of Formulas (I) and/or (Ia) and/or of the carbonyl/imine compounds with the additives, conventionally used for such preparations.

Conventional additives in dyeing agents, used in the form of solutions, creams, emulsions, gels or foams are, for example, solvents such as water, low molecular weight aliphatic alcohols, such as ethanol, n-propanol and isopropanol or glycols such as glycerin and 1,2-propylene glycol, furthermore, wetting agents or emulsifiers from the classes of anionic, cationic, amphoteric or nonionic surface active substances, such as fatty alcohol sulfates, ethoxylated fatty alcohol sulfates, alkyl sulfonates, alkylbenzenesulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty esters, furthermore thickening agents such as higher molecular weight alcohols, starch or cellulose derivatives, perfumes, hair pre-treatment agents, conditioners, hair swelling agents, preservatives, furthermore Vaseline, paraffin oil and fatty acids, as well as, furthermore, care materials such as cationic resins, lanoline derivatives, cholesterol, pantothenic acid and betaine. The components mentioned are used in amounts conventional for such purposes. For example, the wetting agents and emulsifiers are used in concentrations of about 0.5 to 30 percent by weight (based on the dye carrier composition), the thickening agents in an amount of about 0.1 to 30 percent by weight (based on the dye carrier composition) and the care materials in a concentration of about 0.1 to 5 percent by weight (of the dye carrier composition).

The pH of the ready-for-use dyeing agent usually is about 3 to 11 and preferably 6 to 11, a pH of 6.5 to 8.5 being particularly preferred. When component (A1), containing the compounds of Formula (I) and/or (Ia) is mixed with the carbonyl/imine-containing component (A2), the pH of the ready-for-use dyeing agent formed depends on the pH of components (A1) and (A2) as well as on the ratio, in which these two components are mixed. If necessary, the pH of the ready-for-use dyeing agent, can be adjusted, after the two components (A1) and (A2) are mixed, to the desired value by the addition of an alkalizing agent or an acid. To adjust the pH of the ready-for-use agent as well as of components (A1) or (A2), alkalizing agents, such as alkanolamines, alkylamines, alkali hydroxides or ammonium hydroxide and alkali carbonates or ammonium carbonate or acids, such as lactic acid, acetic acid, tartaric acid, phosphoric acid, hydrochloric acid, citric acid, ascorbic acid and boric acid can be used.

The ready-for-use dyeing agent is prepared immediately before use by mixing components (A1), containing the compounds of Formulas (I) and/or (Ia) with the component (A2), containing the carbonyl/imine compounds, optionally with addition of an alkalizing agent or an acid, and then applied on the fibers. Depending on the depth of color desired, this mixture is allowed to act for 5 to 60 minutes and preferably for 15 to 30 minutes at a temperature of 20° to 50° C. and especially of 30° to 40° C. Subsequently, the fibers are washed with water and optionally with a shampoo.

The inventive dyeing agent enables the fibers, especially keratin fibers, such as hair to be dyed gently, uniformly and durably over a wide range of colors. Depending on the compounds of Formula (I)/(Ia) used, outstanding blue colorations can also be achieved. Surprisingly, the dyeings, so obtained, can be removed again completely, rapidly and gently at any time by a reducing agent.

A further object of the present invention therefore is a method for dyeing and later decolorizing keratin fibers, such as wool, silk or hair and especially human hair, for which the fibers are dyed with an inventive dyeing agent (A), the dyeing being removed once again at a later time with a decolorizing agent (B), the component (B) containing at least one sulfite, such as ammonium sulfite, alkali sulfite or an alkaline earth sulfite, especially sodium sulfite or ammonium sulfite, as decolorizing agent.

The total amount of sulfites in component (B) is about 0.1 to 10 percent by weight and preferably about 2 to 5 percent by weight.

The agent for decolorizing the fibers, dyed with the dyeing agent (A), referred to hereinafter as "decolorizing agent", may be an aqueous or aqueous-alcoholic solution, a gel, a cream, an emulsion or a foam. The decolorizing agent can be produced in the form of a one-component as well as in the form of a multi-component preparation. The decolorizing agent may be produced in powder form, or as protection against dust, also as tablets, including effervescent tablets, or as a granulate. Before use, the decolorizing agent is prepared from this with cold or warm water, optionally with the addition of one or more processing aids, which are named in the following. It is, however, also possible that these processing aids, if they exist in solid form, are already contained in the decolorizing powder or granulate or the effervescing tablet. If necessary, dust formation can be decreased by wetting the powder with oils or waxes.

The decolorizing agent may contain additional processing aids such as solvents like water, low molecular weight aliphatic alcohols, such as ethanol, n-propanol, and isopropanol, glycol ethers or glycols such as glycerin and, in particular, 1,2-propylene glycol, furthermore wetting agents or emulsifiers from the class of anionic, cationic, amphoteric or nonionic surface-active substances, such as fatty alcohol sulfates, ethoxylated fatty alcohol sulfates, alkyl sulfonates, alkylbenzenesulfonates, alkyltrimethylamonium salts, alkylbetaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty esters, furthermore, thickeners such as higher molecular weight fatty alcohols, starch or cellulose derivatives, perfumes, hair pre-treatment agents, conditioners, hair-swelling agents, preservatives, Vaseline, paraffin oil and fatty acids, as well as care materials such as cationic resins, lanoline derivatives, cholesterol, pantothenic acid and betaine.

The pH of the decolorizing agent is about 3 to 8 and especially about 4 to 7. If necessary, the pH can be adjusted to the desired value by the additional suitable acids, such as α-hydroxycarboxylic acid, such as lactic acids, tartaric acid, citric acid, or malic acids, phosphoric acid, acetic acid, glycolic acid, salicylic acid, glutathione or gluconic acid lactone, or of alkalizing agents such as alkanolamines, alkylamines, alkali hydroxides, ammonium hydroxide, alkali carbonates, ammonium carbonates or alkali phosphates.

Depending on the dyeing, which is to be decolorized, and on the temperature (about 20° to 50° C.), the period of action of the decolorizing agent is 5 to 60 minutes and especially 15 to 30 minutes. The decolorizing process can be accelerated by supplying heat. At the end of the period of action of the decolorizing agent, the hair is rinsed with water and optionally washed with a shampoo.

Although component (B) is particularly suitable for decolorizing keratin fibers, especially human hair, dyed with the dyeing agent (A), it can, in principle, also be used to decolorize other natural or synthetic fibers, such as cotton, viscose nylon and cellulose acetate, dyed with dyeing agent (A).

A further object of the present application are compounds of Formula (I) or (Ia), in which R2' or R2 is a methylene or methyl group, when R10 is hydrogen or a methoxy group, and at least one of the R5 to R12 groups is different from hydrogen, when the R1, R3 and R4 simultaneously represent a methyl group; as well as compounds of Formula (V).

The following examples are intended to explain the object in greater detail, without limiting it to these examples,

EXAMPLES

Examples 1.1 to 1.22

Synthesis of Indoline Derivatives of Formula (I)/(Ia)

A) General Procedure for Synthesizing 3H-indole Derivatives of Formula (VII)

Variation 1:

5-Halogeno-2,3,3-trimethyl-3H-indole (1 mole) of Formula (II) and 1.3 moles of aryl boric acid of Formula (III)

are dissolved in 1,2-dimethoxyethane. Argon is bubbled through this solution for 15 minutes. Subsequently, the palladium catalyst (0.1 to 0.12 moles) and 2 to 2.6 moles of potassium carbonate dissolved in water are added. The reaction mixture is refluxed for 2 to 6 hours in an argon atmosphere. At the end of the reaction, the reaction mixture is filtered through silica gel and taken up in dichloromethane and the resulting organic phase is washed twice with 1M sodium hydroxide solution and 3 times with water, dried over magnesium sulfate and subsequently evaporated under reduced pressure at 40° C. The residue is distilled under a high vacuum or purified chromatographically.

Variation 2:

5-Dioxoborinane-2,3,3-trimethyl-3H-indole (1 mole) of Formula (V) and 1.0 to 1.3 moles of the aryl halide compound of Formula (VI) are dissolved in 1,2-dimethoxyethane. Argon is bubbled for 15 minutes through this solution. Subsequently, the palladium catalyst (0.1 to 0.2 moles) and 2 to 2.6 moles of potassium carbonate, dissolved in water, are added. The reaction mixture is refluxed for 2 to 6 hours in an argon atmosphere. At the end of the reaction, the reaction mixture is filtered through silica gel and taken up in dichloromethane and the resulting organic phase is washed twice with 1M sodium hydroxide solution, twice with water, and once with a saturated salt solution, and dried over magnesium sulfate and subsequently evaporated under reduced pressure at 40° C. The residue is distilled under a high vacuum or purified chromatographically.

Variation 3:

Aryl halogen compound (1.95 moles), 0.15 moles of palladium catalyst and 3.9 moles of an aqueous potassium carbonate solution are added to 1.5 moles of 5-dioxaborinane-2,3,3-trimethyl-3H-indol of Formula (V), dissolved 1,2-dimethoxyethane. Subsequently, the reaction mixture is mixed with argon, heated to 80° C. and rotated at 360 elliptical cycles per minute. The course of the reaction is monitored by thin-layer chromatography (silica gel; hexane/ethanol or hexane/acetone). At the end of the reaction (after about 4 to 10 hours, the aqueous phase is removed and the product, dissolved in the organic phase, absorbed on silica gel and purified chromatographically (silica gel; hexane/ethanol).

B.) General Procedure for Synthesizing 5-Dioxaborinane-2,3,3-trimethyl-3H-indole Derivatives of Formula (IV)

The aryl halogen compound (1 mole) of Formula (II) and 1.5 moles of diboron compound of Formula (IV) as well as the palladium catalyst (0.03 to 0.05 moles) and 3 to 3.2 moles of potassium acetate are added to anhydrous dioxane. The reaction mixture subsequently is heated for 4 to 6 hours with vigorous stirring in an atmosphere of nitrogen to a temperature of 80° to 85° C. Subsequently, the reaction solution is mixed with water and extracted 3 times with ethyl acetate. The combined organic phases are washed once with saturated salt solution and twice with distilled water, then dried over magnesium sulfate and concentrated to dryness under reduced pressure at 40° C. The residue is purified chromatographically (silica gel, hexane/acetone or by means of ball tube distillation.

C.) General Procedure for the N-alkylation of 3H-Indole Derivatives of Formula (VII)

Variation 1:

The intermediate (1 mole) obtained in step A) is dissolved in 1,2-dichloroethane, treated with 1.2 moles of trimethyloxonium tetrafluoroborate and refluxed for 6 hours. The product precipitates if the reactions mixture is cooled to 4° C. or if ethyl acetate or t-butyl methyl ether is added. The solid obtained is filtered off, washed with a little ethyl acetate or t-butyl methyl ether and recrystallized from methanol, ethanol, acetonitrile or ethyl acetate.

Variation 2:

The intermediate (1 mole), obtained in step A) is dissolved in chloroform and treated with 1.1 to 2.1 moles of methyl iodide. The solution obtained is then stirred for 24 hours at 25° C. with exclusion of light and under a blanket of argon. Subsequently, t-butyl methyl ether is added to this solution and the yellow precipitate is filtered off with suction and recrystallized from ethanol.

Variation 3:

The intermediate (1 mole), obtained in step A), is dissolved in 1,2-dichloroethane. Triethyloxonium tetrafluoroborate (1 to 2.5 moles), dissolved in 1,2-dichloroethane, is then added. The reaction mixture subsequently is heated to 80° C. and stirred with 360 elliptical cycles per minute. The course the reaction is followed by a thin-layer chromatography (silica gel, ethyl acetate or butanol/acetic acid/water 50:15:35). At the end of the reaction, after about 6 hours, the reaction mixture is concentrated under reduced pressure to a viscous oil, which, upon being mixed with ethanol or ethyl acetate, forms a precipitate. The precipitated product is filtered off, washed and dried at 40°.

Example 1.1

5-(2,4-Dimethoxyphenyl)-1,2,3,3-tetramethyl-3H-indole-1-ium-tetrafluoroborate

The synthesis is carried out according to variation 1 of the general synthesis procedure A), 0.92 g of 5-bromo-2,3,3-trimethyl-3H-indole and 1.01 g of 2,4-dimethoxyphenylboric acid in 20 mL of 1,2 dimethoxyethane and 0.51 g of tetrakis(triphenylphosphine)palladium(0) and 1.38 g of potassium carbonate in 5 g of water being used.

The resulting residue is purified by chromatography (silica gel, hexane/ethyl acetate 4/6), 0.86 g (76% of the theoretical yield) of 5-(2,4-dimethoxyphenyl)-2,3,3-trimethyl-3H-indole being obtained.

The 5-(2,4-dimethoxyphenyl)-2,3,3-trimethyl-3H-indole (0.82 g), so obtained, is alkylated, as described in variation 1 of the general procedure C), with 0.49 g of trimethyloxonium tetrafluoroborate in 5 mL of 1,2-dichloroethane. The crude product is recrystallized from methanol.

Yield: 0.61 g (55% of the theoretical) 5-(2,4-dimethoxyphenyl)-1,2,3,3-tetramethyl-3H-indole-1-ium-tetrafluoroborate Melting point: 184–187° C.

$^1$H-NMR ($D_6$-DMSO): δ=1.53 ppm (s, 6H); 2.75 ppm (s, 3H); 3.77 ppm (s, 3H); 3.81 ppm (s, 3H); 3.97 ppm (s, 3H); 6.65 ppm (d, $^3$J=8 Hz, 1H); 6.70 ppm (s, 1H); 7.29 ppm (d, $^3$J=8 Hz, 1H); 7.66 ppm (d, $^3$J=9 Hz); 7.84 ppm (s, 1H); 7.85 ppm (d, $^3$J=9Hz, 1H).

FAB Mass Spectrum: $M^+$=310.2 (100% relative intensity)

Elementary Analysis:

| ($C_{20}H_{24}NO_2BF_4$) |  | % C | % H | % N | % F | % O |
|---|---|---|---|---|---|---|
|  | calc.: | 60.48 | 6.09 | 3.53 | 19.13 | 8.06 |
|  | found: | 60.20 | 6.30 | 3.40 | 18.80 | 8.20 |

Example 1.2

5-(1,3-Benzodioxol-5-yl)-1,2,3,3-Tetramethyl-3H-indol-1-ium tetrafluoroborate The synthesis proceeds according to variation 1 of the general synthesis procedure A), 0.92 g of 5-bromo-2,3,3-trimethyl-3H-indole and 0.83 g of 3,4-methylenedioxyphenylboric acid in 20 mL of 1,2 dimethoxyethane and 0.51 g of tetrakis(triphenylphosphine)palladium(0) and 1.38 g of potassium carbonate in 5 g of water being used.

The resulting residue is purified by chromatography (silica gel, hexane/ethyl acetate 4/6), 0.89 g (83% of the theoretical yield) of 5-(1,3-benzodioxol-5-yl)-2,3,3-trimethyl-3H-indole being obtained.

The 5-(1,3-benzodioxol-5-yl)-2,3,3-trimethyl-3H-indole (0.70 g), so obtained, is alkylated, as described in variation 1 of the general procedure C), with 0.44 g of trimethyloxonium tetrafluoroborate in 4 mL of 1,2-dichloroethane. The crude product is recrystallized from 1:1 ethyl acetate/acetonitrile.

Yield: 0.65 g (68% of the theoretical) 5-(1,3-benzodioxol-5-yl)-1,2,3,3-tetramethyl-3H-indole-1-ium-tetrafluoroborate $^1$H-NMR (D$_6$-DMSO): δ=1.55 ppm (s, 6H); 2.75 ppm (s, 3H); 3.97 ppm (s, 3H); 6.10 ppm (s, 2H); 7.05 (d, $^3$J=8 Hz, 1H); 7.28 ppm (d, $^3$J=8 Hz, 1H); 7.40 ppm (s, 1H); 7.86 ppm (d, $^3$J=9 Hz, 1H); 7.91 ppm (d, $^3$J=9 Hz, 1H); 8.11 (s, 1H).

FAB Mass Spectrum: M$^+$=294.30

Elementary Analysis:

| (C$_{19}$H$_{20}$NO$_2$BF$_4$) | % C | % H | % N | % F | % O |
|---|---|---|---|---|---|
| calc.: | 59.87 | 5.29 | 3.67 | 19.94 | 8.39 |
| found: | 59.60 | 5.40 | 3.70 | 19.90 | 8.20 |

Example 1.3

1,2,3,3-Tetramethyl-5-(-2-trifluoromethyl)phenyl)-3H-indole-1-ium tetrafluoroborate The synthesis proceeds according to variation 1 of the general synthesis procedure A), 0.92 g of 5-bromo-2,3,3-trimethyl-3H-indole and 0.95 g of 2-trifluoromethylphenylboric acid in 20 mL of 1,2 dimethoxyethane and 0.51 g of tetrakis(triphenylphosphine)palladium(0) and 1.38 g of potassium carbonate in 5 g of water being added.

The resulting residue is purified by chromatography (silica gel, hexane/ethyl acetate 4:6), 0.77 g (66% of the theoretical yield) of 5-(2-(trifluoromethyl)phenyl)-2,3,3-trimethyl-3H-indole being obtained.

The 5-(2-(trifluoromethyl)phenyl)-2,3,3-trimethyl-3H-indole (0.76 g), so obtained, is alkylated, as described in variation 1 of the general procedure C), with 0.44 g of trimethyloxonium tetrafluoroborate in 4 mL of 1,2-dichloroethane. The crude product is recrystallized from ethanol.

Yield: 0.46 g (46% of the theoretical) 1,2,3,3-tetramethyl-5-(-2-trifluoromethyl)phenyl)-3H-indole-1-ium-tetrafluoroborate $^1$H-NMR (D$_6$-DMSO): δ=1.54 ppm (s, 6H); 2.77 ppm (s, 3H); 3.99 ppm (s, 3H); 7.40–8.05 ppm (m, 7H)

FAB Mass Spectrum: M$^+$=318.0 (100% relative intensity)

Example 1.4

1,2,3,3-Tetramethyl-5-(thiophene-3-yl)-3H-indolium iodide

The synthesis proceeds according to variation 1 of the general synthesis procedure A), 1 g of 5-bromo-2,3,3-trimethyl-3H-indole and 0.70 g of 3-thiopheneboric acid in 18 mL of 1,2-dimethoxyethane, as well as 0.56 g of tetrakis (triphenylphosphine)palladium(0) and 1.51 g of potassium carbonate in 5.3 g of water being used.

The resulting residue is purified by chromatography (silica gel, hexane/ethyl acetate 4:6), 0.81 g (80% of the theoretical yield) of 5-(thiophene-3-yl)-2,3,3-trimethyl-3H-indole being obtained.

The 5-(thiophene-3-yl)-2,3,3-trimethyl-3H-indole (1.03 g), so obtained, is alkylated, as described in variation 2 of the general procedure C), with 0.7 g of methyl iodide in 4 mL of chloroform.

Yield: 0.37 g (23% of the theoretical) 1,2,3,3-tetramethyl-5-(thiophene-3-yl)-3H-indolium iodide $^1$H-NMR (CD$_3$-OD): δ=1.65 ppm (s, 6H); 4.06 ppm (s, 3H); 4.85 ppm (s, 3H); 7.53–7.59 ppm (m, 2H); 7.81–7.86 ppm (m, 2H); 7.93 ppm (dd, $^3$J=8.5 Hz, $^4$J=2 Hz, 1H); 8.07 ppm (d, $^4$J=2 Hz, 1H)

FAB Mass Spectrum: M$^+$=256.0 (100% relative intensity)

Elementary Analysis:

| (C$_{16}$H$_{18}$NSI) | % C | % H | % N |
|---|---|---|---|
| calc.: | 50.14 | 4.73 | 3.65 |
| found: | 50.14 | 4.80 | 3.35 |

Example 1.5

5-Phenyl-1,2,2,3-tetramethyl-1(3H)-indolium tetrafluoroborate

The synthesis proceeds according to variation 1 of the general synthesis procedure A), 1 g of 5-bromo-2,3,3-trimethyl-3H-indole and 0.69 g of benzeneboric acid in 18 mL of 1,2-dimethoxyethane, as well as 0.56 g of tetrakis(triphenyl-phosphine)palladium(0) and 1.5 g of potassium carbonate in 5.3 g of water being used.

The resulting residue is purified by chromatography (silica gel, hexane/ethyl acetate 4:6), 0.81 g (82% of the theoretical yield) of 5-phenyl-2,3,3-trimethyl-3H-indole being obtained.

The 5-phenyl-2,3,3-trimethyl-3H-indole (1.5 g), so obtained, is alkylated, as described in variation 1 of the general procedure C), with 1.11 g of trimethyloxonium tetrafluoroborate in 5 mL of 1,2-dichloroethane. The crude product is recrystallized from acetonitrile.

Yield: 1.33 g (63% of the theoretical) 5-phenyl-1,2,2,3-tetramethyl-1(3H)-indolium-tetrafluoroborate $^1$H-NMR (D$_6$-DMSO): δ=1.57 ppm (s, 6H); 2.76 ppm (s, 3H); 3.99 ppm (s, 3H); 7.35–7.60 ppm (m, 3H); 7.70–7.83 ppm (m; 2H); 7.88–8.02 ppm (m, 2H); 8.17 ppm (s, 1H)

FAB Mass Spectrum: M$^+$=250.3 (100% relative intensity)

Elementary Analysis:

| (C$_{18}$H$_{20}$NBF$_4$) |  | % C | % H | % N | % F |
|---|---|---|---|---|---|
|  | calc.: | 64.12 | 5.98 | 4.15 | 22.54 |
|  | found: | 63.60 | 6.10 | 4.20 | 22.50 |

Example 1.6

1,2,3,3-Tetramethyl-5-p-tolyl-3H-indolium tetrafluoroborate

The synthesis proceeds according to variation 2 of the general synthesis procedure A), 2.20 g of 5-(5,5-dimethyl-(1,3,2)dioxaborinane-2-yl)-2,3,3-trimethyl-3H-indole and 1.8 g of 4-bromotoluene in 50 mL of 1,2-dimethoxyethane with 0.94 g of tetrakis(triphenylphosphine)palladium(0) and 2.90 g of potassium carbonate in 10.5 g of water being used.

The resulting residue is distilled by ball tube distillation under vacuum (0.004 mbar) at 107° C., 1.80 g (90% of the theoretical yield) of 2,3,3-trimethyl-5-p-tolyl-3H-indole being obtained.

The 2,3,3-trimethyl-5-p-tolyl-3H-indole (1.7 g), so obtained, is alkylated, as described in variation 1 of the general synthesis procedure C), with 1.27 g of trimethyloxonium tetrafluoroborate in 6 mL of 1,2-dichloroethane. The crude product is recrystallized from methanol.

Yield: 1.43 g (57% of the theoretical) 1,2,3,3-tetramethyl-5-p-tolyl-3H-indolium-tetrafluoroborate $^1$H-NMR (D$_6$-DMSO): δ=1.57 ppm (s, 6H); 2.36 ppm (s, 3H); 2.76 ppm (s, 3H); 3.98 ppm (s, 3H); 7.32 ppm (~d, $^3$J~8 Hz, 2H); 7.68 ppm (~d, $^3$J~8 Hz, 2H); 7.88 ppm (~d, $^3$J~9 Hz, 1H); 7.94 ppm (~d, $^3$J~9 Hz, 1H); 8.14 ppm (s, 1H)

FAB Mass Spectrum: M$^+$=264.1 (100% relative intensity)

Elementary Analysis:

| (C$_{19}$H$_{22}$NBF$_4$) |  | % C | % H | % N | % F |
|---|---|---|---|---|---|
|  | calc.: | 64.98 | 6.31 | 3.99 | 21.64 |
|  | found: | 64.90 | 6.20 | 3.90 | 21.50 |

Example 1.7

1,2,3,3-Tetramethyl-5-naphthalene-1-yl-3H-indolium tetrafluoroborate

The synthesis proceeds according to variation 1 of the general synthesis procedure A), 1.06 g of 5-bromo-2,3,3-trimethyl-3H-indole and 1.0 g of naphthalene-1-boric acid in 20 mL of 1,2-dimethoxyethane, as well as 0.57 g of tetrakis (triphenyl-phosphine)palladium(0) and 1.6 g of potassium carbonate in 5.8 g of water being used.

The resulting residue is distilled by ball tube distillation under vacuum (0.008 mbar) at 200° C., 0.78 g (61% of the theoretical yield) of 2,3,3-trimethyl-5-naphthalene-1-yl-3H-indole being obtained.

The 2,3,3-trimethyl-5-naphthalene-1-yl-3H-indole (0.65 g), so obtained, is alkylated, as described in variation 1 of the general synthesis procedure C), with 0.4 g trimethyloxonium tetrafluoroborate in 5 mL of 1,2-dichloroethane. The reaction mixture is concentrated under reduced pressure. The oily residue is taken up in a little CH$_2$Cl$_2$ and the product is precipitated by the addition of t-butyl methyl ether.

Yield: 0.32 g (36% of the theoretical) 1,2,3,3-tetramethyl-5-naphthalene-1-yl-3H-indolium-tetrafluoroborate $^1$H-NMR (CD$_3$-OD): δ=1.61 ppm (s, 6H); 2.82 ppm (s, 3H); 4.06 ppm (s, 3H); 7.40–7.70 ppm (m, 4H); 7.70–7.85 ppm (m; 2H); 7.95–8.15 ppm (m, 4H)

FAB Mass Spectrum: M$^+$=300.0 (100% relative intensity)

Example 1.8

2,3,3-Trimethyl-5-(4,4,5,5-tetramethyl-[1,3,2]dioxaborolan-2-yl)-3H-indole

The synthesis proceeds according to the general synthesis procedure B), 0.16 g of 5-bromo-2,3,3-trimethyl-3H-indole, 0.25 g of bis(pinacolato)-diboron, 0.02 g (1,1'-bis(diphenylphosphine)-ferrocene)dichloro-palladium(II) and 0.2 g of potassium acetate in 10 mL of dioxane being used.

The resulting residue is purified chromatographically (silica gel, hexane/acetone=9/1), a yield of 0.13 g (68% of the theoretical yield) of 2,3,3-trimethyl-5-(4,4,5,5-tetramethyl-(1,3,2)dioxaborolane-2-yl)-3H-indole being obtained.

$^1$H-NMR (CDCl$_3$) δ=1.31 ppm (s, 6H); 1.36 ppm (s, 12H); 2.30 ppm (s, 3H); 7.53 ppm (d, $^3$J=8 Hz, 1H); 7.73 ppm (s, 1H); 7.79 ppm (d, $^3$J=8 Hz, 1H);

EI Mass Spectrum: 285 (100, M$^+$); 270 (53); 228 (7); 212 (10); 199 (62); 186 (62) 170 (18); 158 (8); 144 (16); 116 (15); 103 (6); 78 (14); 60 (14)

Example 1.9

5-(5,5-Dimethyl-[1,3,2]-dioxaborinane-2-yl)-2,3,3-trimethyl-3H-indole

The synthesis proceeds according to the general synthesis procedure B), 11.91 g of 5-bromo-2,3,3-trimethyl-3H-indole, 16.94 g of bis(neopentyl glycolato) diboron, 1.10 g (1,1'-bis(diphenylphosphino)-ferrocene)dichloro-palladium (II) and 15.21 g of potassium acetate in 150 mL of dioxane being used.

The resulting oily residue is purified by ball tube distillation (0.020 mbar, 160° to 170° C.

Yield: 9.50 g (70% of the theoretical) 5-(5,5-dimethyl-[1,3,2]-dioxaborinane-2-yl)-2,3,3-trimethyl-3H-indole $^1$H-NMR (CDCl$_3$): δ=1.03 ppm (s, 6H); 1.31 ppm (s, 6H); 2.30 ppm (s, 3H); 3.78 ppm (s, 4H); 7.52 ppm (d, $^3$J=8 Hz, 1H); 7.73 ppm (s, 1H); 7.78 ppm (d, $^3$J=8 Hz, 1H).

EI Mass Spectrum: 271 (100, M$^+$); 256 (68); 230 (5); 184 (18); 170 (42); 144 (46) 129 (19); 115 (36); 91 (13); 77 (26); 57 (19)

Example 1.10:

1-Ethyl-2,3,3-trimethyl-5-(4-methylsulfurnyl-phenyl)-3H-indolium tetrafluoroborate The synthesis proceeds according to variation 3 of the general synthesis procedure A), 407 mg of 5-(5,5-dimethyl-(1,3,2)dioxaborinane-2-yl)-2,3,3-trimethyl-3H-indole, and 396 mg of 4-bromothianisole in 7.5 ml of 1,2-dimethoxyethane, as well as 173 mg of tetrakis(triphenylphosphine) palladium(0) and 2.0 mL of potassium carbonate solution (2.76 g of potassium carbonate in 10 mL of water) being used.

The resulting residue is purified chromatographically (silica gel, hexane/ethanol 9:1).

2,3,3-Trimethyl-5-(4-methylsulfanyl-phenyl)-3H-indole is obtained in a yield of 219 mg (52% of the theoretical).

The 2,3,3-trimethyl-5-(4-methylsulfanyl-phenyl)-3H-indole (219 mg, so obtained, is alkylated according to variation 3 of the general synthesis method C) with 1.1 mL of 1,2-dichloroethane and 0.93 mL of a triethyloxonium tetrafluoroborate solution (=1.90 g of triethyloxonium tetrafluoroborate in 10 mL of 1,2-dichloroethane).

The product, so obtained, is washed once with hot ethanol and once with methanol.

Yield: 171 mg (55% of the theoretical) 1-ethyl-2,3,3-trimethyl-5-(4-methylsulfurnyl-phenyl)-3H-indolium-tetrafluoroborate $^1$H-NMR (D$_6$DMSO): δ=1.45 ppm (t, $^3$J=7 Hz, 3H); 1.57 ppm (s, 6H); 2.52 ppm (s, 3H); 2.82 ppm (s, 3s, 3H); 4.50 ppm (q, $^3$J=7 Hz, 2H); 7.39 ppm (d, $^3$J=8 Hz, 2H); 7.73 ppm (d, $^3$J=8 Hz, 2H); 7.90 ppm (d, $^3$J~8 Hz, 1H); 8.00 ppm (d, $^3$J=8 Hz, 1H); 8.17 ppm (s, 1H).

ESI Mass Spectrum: M$^+$=310.1 (100% relative intensity) [M+Na]=332.1 (20% relative intensity)

Example 1.11

1'-Acetyl-1-ethyl-2,3,3-trimethyl-2',3'-dihydro-3H-1'H-[5,5']biindolyl-1-ium tetrafluoroborate The synthesis proceeds according to variation 3 of the general synthesis procedure A), 407 mg of 5-(5,5-dimethyl-(1,3,2)dioxaborinane-2-yl)-2,3,3-trimethyl-3H-indole, and 468 mg of 1-acetyl-5-bromoindoline in 7.5 ml of 1,2-dimethoxythane, as well as 173 mg of tetrakis(triphenylphosphine)palladium(0) and 2.0 mL of potassium carbonate solution (2.76 g of potassium carbonate in 10 mL of water) being used.

The resulting residue is purified chromatographically (silica gel, hexane/ethanol 8:2).

1-(2',3',3'-Trimethyl-2,3-dihydro-3'H-(5,5')biindolyl-1-yl)-ethanone is obtained in a yield of 242 mg (51% of the theoretical).

The 1-(2',3',3'-trimethyl-2,3-dihydro-3'H-(5,5')biindolyl-1-yl)-ethanone (242 mg), so obtained, is alkylated according to variation 3 of the general synthesis method C) with 1.2 mL of 1,2-dichloroethane and 0.91 mL of a triethyloxonium tetrafluoroborate solution (=1.90 g of triethyloxonium tetrafluoroborate in 10 mL of 1,2-dichloroethane).

The product, so obtained, is washed with hot ethanol.

Yield: 190 mg (58% of the theoretical) 1'-acetyl-1-ethyl-2,3,3-trimethyl-2',3'-dihydro-3H-1'H-[5,5']biindolyl-1-ium tetrafluoroborate $^1$H-NMR (D$_6$DMSO): δ=1.45 ppm (t, $^3$J=7 Hz, 3H); 1.57 ppm (s, 6H); 2.18 ppm (s, 3H); 2.82 ppm (s, 3H); 3.22 ppm (t, $^3$J~8 Hz, 2H); 4.15 ppm (t, $^3$J~8 Hz, 2H); 4.50 ppm (q, $^3$J=7 Hz, 2H); 7.58 ppm (d, $^3$J~9 Hz, 1H); 7.68 ppm (s, 1H); 7.87 ppm (d, $^3$J~8 Hz, 1H); 7.98 ppm (d, $^3$J~8 Hz, 1H); 8.12 ppm (d, $^3$J~9 Hz, 1H); 8.16 ppm (s, 1H).

ESI Mass Spectrum: M$^+$=347.2 (100% relative intensity) [M+Na]=369.1 (93% relative intensity)

Example 1.12

1-Ethyl-2,3,3-trimethyl-5-naphthalene-2-yl-3H-indolium tetrafluoroborate

The synthesis proceeds according to variation 3 of the general synthesis procedure A), 407 mg of 5-(5,5-dimethyl-(1,3,2)dioxaborinane-2-yl)-2,3,3-trimethyl-3H-indole and 404 mg of 2-bromo-naphthalene in 7.5 ml of 1,2-dimethoxythane, as well as 173 mg of tetrakis(triphenylphosphine)palladium(0) and 2.0 mL of potassium carbonate solution (2.76 g of potassium carbonate in 10 mL of water) being used.

The resulting residue is purified chromatographically (silica gel, hexane/ethanol 9:1).

2,3,3-Trimethyl-5-napthalene-2-yl-3H-indole is obtained in a yield of 256 mg (60% of the theoretical).

The 2,3,3-trimethyl-5-napthalene-2-yl-3H-indole (256 mg), so obtained, is alkylated according to variation 3 of the general synthesis method C) with 1.3 mL of 1,2-dichloroethane and 1.08 mL of a triethyloxonium tetrafluoroborate solution (=1.90 g of triethyloxonium tetrafluoroborate in 10 mL of 1,2-dichloroethane). The product, so obtained, is washed with ethanol.

Yield: 244 mg (68% of the theoretical) 1-ethyl-2,3,3-trimethyl-5-naphthalene-2-yl-3H-indolium tetrafluoroborate $^1$H-NMR (D$_6$DMSO): δ=1.48 ppm (t, $^3$J=7 Hz, 3H); 1.61 ppm (s, 6H); 2.85 ppm (s, 3H); 4.53 ppm (q, $^3$J=7 Hz, 2H); 7.53–7.68 ppm (m, 2H); 7.92–8.17 ppm (m, 6H); 8.35 ppm (s, 2H).

ESI Mass Spectrum: M$^+$=314.1 (100% relative intensity) [M+Na]=336.1 (27% relative intensity)

Example 1.13

1-Ethyl-5-(6-hydroxy-naphthalene-2-yl)-2,3,3-trimethyl-3H-indolium tetrafluoroborate The synthesis proceeds according to variation 3 of the general synthesis procedure A), 407 mg of 5-(5,5-dimethyl-(1,3,2)dioxaborinane-2-yl)-2,3,3-trimethyl-3H-indole, and 435 mg of 6-bromo-2-naphthol in 7.5 ml 1,2-dimethoxythane, as well as 173 mg of tetrakis(triphenylphosphine)palladium(0) and 2.0 mL of potassium carbonate solution (2.76 g of potassium carbonate in 10 mL of water) being used.

The resulting residue is purified chromatographically (silica gel, hexane/ethanol 8:2).

6-(2,3,3-Trimethyl-3H-indole-5-yl)-napthalene-2-ol is obtained in a yield of 427 mg (94% of the theoretical).

The 6-(2,3,3-trimethyl-3H-indole-5-yl)-napthalene-2-ol (427 mg), so obtained, is alkylated according to variation 3 of the general synthesis method C) with 4.1 mL of 1,2-dichloroethane and 1.70 mL of a triethyloxonium tetrafluoroborate solution (=1.90 g of triethyloxonium tetrafluoroborate in 10 mL of 1,2-dichloroethane). The product, so obtained, is washed with ethyl acetate.

Yield: 194 mg (33% of the theoretical) 1-ethyl-5-(6-hydroxy-naphthalene-2-yl)-2,3,3-trimethyl-3H-indolium tetrafluoroborate $^1$H-NMR (D$_6$DMSO): δ=1.48 ppm (m, 9H); 2.54 ppm (s, 3H); 4.52 ppm (m, 2H); 7.11–7.14 ppm (m, 2H); 7.63 ppm (d, $^3$J=8 Hz, 1H); 7.78–7.76 ppm (m, 4H); 8.07 ppm (s, 1H); 8.13 ppm (2, 1H).

ESI Mass Spectrum: M$^+$=330.1 (100% relative intensity)

Example 1.14

5-Anthracene-9-yl-1-ethyl-2,3,3-trimethyl-3H-indolium tetrafluoroborate

The synthesis proceeds according to variation 3 of the general synthesis procedure A), 407 mg of 5-(5,5-dimethyl-(1,3,2)dioxaborinane-2-yl)-2,3,3-trimethyl-3H-indole, and 501 mg of 9-bromo-anthracene in 7.5 ml of 1,2-dimethoxythane, as well as 173 mg of tetrakis(triphenylphosphine)

palladium(0) and 2.0 mL of potassium carbonate solution (2.76 g of potassium carbonate in 10 mL of water) being used. The resulting residue is purified chromatographically (silica gel, hexane/ethanol 9:1).

5-Anthracene-9-yl-2,3,3-trimethyl-3H-indole is obtained in a yield of 251 mg (50% of the theoretical).

The 5-anthracene-9-yl-2,3,3-trimethyl-3H-indole (251 mg), so obtained, is alkylated according to variation 3 of the general synthesis method C) with 1.3 mL of 1,2-dichloroethane and 0.90 mL of a triethyloxonium tetrafluoroborate solution (=1.90 g of triethyloxonium tetrafluoroborate in 10 mL of 1,2-dichloroethane). The product, so obtained, is washed with ethanol.

Yield: 179 mg (53% of the theoretical) 5-anthracene-9-yl-1-ethyl-2,3,3-trimethyl-3H-indolium tetrafluoroborate $^1$H-NMR (D$_6$DMSO): δ=1.54–1.61 ppm (m, 9H); 2.90 ppm (s, 3H); 4.61 ppm (q, $^3$J=7 Hz, 2H); 7.47–7.58 ppm (m, 6H); 7.69 ppm (d, $^3$J=8 Hz, 1H); 7.97 ppm (s, 1H); 8.18–8.23 ppm (m, 3H); 8.75 ppm (s, 1H).

ESI Mass Spectrum: M$^+$=364.2 (100% relative intensity) [M+Na]=386.1 (33% relative intensity)

Example 1.15

5-(3,5-Dimethyl-phenyl)-1-ethyl-2,3,3-trimethyl-3H-indolium tetrafluoroborate

The synthesis proceeds according to variation 3 of the general synthesis procedure A), 407 mg of 5-(5,5-dimethyl-(1,3,2)dioxaborinane-2-yl)-2,3,3-trimethyl-3H-indole, and 361 mg of 1-bromo-3,5-dimethylbenzene in 7.5 ml of 1,2-dimethoxythane, as well as 173 mg of tetrakis(triphenylphosphine)palladium(0) and 2.0 mL of potassium carbonate solution (2.76 g of potassium carbonate in 10 mL of water) being used. The resulting residue is purified chromatographically (silica gel, hexane/ethanol 9:1).

5-(3,5-Dimethyl-phenyl)-2,3,3-trimethyl-3H-indole is obtained in a yield of 193 mg (49% of the theoretical).

The 5-(3,5-dimethyl-phenyl)-2,3,3-trimethyl-3H-indole (193 mg), so obtained, is alkylated according to variation 3 of the general synthesis method C) with 1.0 mL of 1,2-dichloroethane and 0.88 mL of a triethyloxonium tetrafluoroborate solution (=1.90 g of triethyloxonium tetrafluoroborate in 10 mL of 1,2-dichloroethane). The product, so obtained, is washed with acetic acid.

Yield: 167 mg (60% of the theoretical) 5-(3,5-dimethyl-phenyl)-1-ethyl-2,3,3-trimethyl-3H-indolium tetrafluoroborate $^1$H-NMR (D$_6$DMSO): δ=1.45 ppm (t, $^3$J=7 Hz, 3H); 1.57 ppm (s, 6H); 2.35 ppm (s, 6H); 2.82 ppm (s, 3H); 4.50 ppm (q, $^3$J=7 Hz, 2H); 7.06 ppm (s, 1H); 7.37 ppm (s, 2H); 7.87 ppm (d, $^3$J=8 Hz, 1H); 8.00 ppm (d, $^3$J=8 Hz, 1H); 8.15 ppm (s, 1H)

ESI Mass Spectrum: M$^+$=292.3 (100% relative intensity)

Example 1.16

5-Acenaphthene-5-yl-1-ethyl-2,3,3-trimethyl-3H-indolium tetrafluoroborate

The synthesis proceeds according to variation 3 of the general synthesis procedure A), 407 mg of 5-(5,5-dimethyl-(1,3,2)dioxaborinane-2-yl)-2,3,3-trimethyl-3H-indole, and 455 mg of 5-bromoacenaphthene in 7.5 ml of 1,2-dimethoxythane, as well as 173 mg of tetrakis(triphenylphosphine)palladium(0) and 2.0 mL of potassium carbonate solution (2.76 g of potassium carbonate in 10 mL of water) being used. The resulting residue is purified chromatographically (silica gel, hexane/ethanol 9:1).

5-Acenaphthacene-5-yl-2,3,3-trimethyl-3H-indole is obtained in a yield of 237 mg (51% of the theoretical).

The 5-acenaphthacene-5-yl-2,3,3-trimethyl-3H-indole (237 mg), so obtained, is alkylated according to variation 3 of the general synthesis method C) with 1.2 mL of 1,2-dichloroethane and 0.91 mL of a triethyloxonium tetrafluoroborate solution (=1.90 g of triethyloxonium tetrafluoroborate in 10 mL of 1,2-dichloroethane). The product, so obtained, is washed with ethanol.

Yield: 108 mg (33% of the theoretical) 5-acenaphthene-5-yl-1-ethyl-2,3,3-trimethyl-3H-indolium tetrafluoroborate $^1$H-NMR (D$_6$DMSO): δ=1.50 ppm (t, $^3$J=7 Hz, 3H); 1.60 ppm (s, 6H); 2.85 ppm (s, 3H); 3.42 ppm (s, 4H); 4.55 ppm (q, $^3$J=7 Hz, 2H); 7.38–7.58 ppm (m, 5H); 7.77 ppm (d, $^3$J=8 Hz, 1H); 8.04 ppm (s, 1H); 8.08 ppm (d, $^3$J=8 Hz, 1H).

ESI Mass Spectrum: M$^+$=340.1 (100% relative intensity) [M+Na]=362.3 (25% relative intensity)

Example 1.17

1-Ethyl-5-(4-methoxy-2-methyl-phenyl)-2,3,3-trimethyl-3H-indolium tetrafluoroborate The synthesis proceeds according to variation 3 of the general synthesis procedure A), 407 mg of 5-(5,5-dimethyl-(1,3,2)dioxaborinane-2-yl)-2,3,3-trimethyl-3H-indole, and 392 mg of 4-bromo-3-methylanisole in 7.5 ml of 1,2-dimethoxythane, as well as 173 mg of tetrakis(triphenylphosphine)palladium(0) and 2.0 mL of potassium carbonate solution (2.76 g of potassium carbonate in 10 mL of water) being used. The resulting residue is purified chromatographically (silica gel, hexane/ethanol 9:1).

5-(4-Methoxy-2-methyl-phenyl)-2,3,3-trimethyl-3H-indole is obtained in a yield of 173 mg (43% of the theoretical).

The 5-(4-methoxy-2-methyl-phenyl)-2,3,3-trimethyl-3H-indole (173 mg), so obtained, is alkylated according to variation 3 of the general synthesis method C) with 0.9 mL of 1,2-dichloroethane and 0.78 mL of a triethyloxonium tetrafluoroborate solution (=1.90 g of triethyloxonium tetrafluoroborate in 10 mL of 1,2-dichloroethane). The product, so obtained, is washed with ethanol.

Yield: 134 mg (52% of the theoretical) 1-ethyl-5-(4-methoxy-2-methyl-phenyl)-2,3,3-trimethyl-3H-indolium tetrafluoroborate $^1$H-NMR (D$_6$DMSO): δ=1.46 ppm (t, $^3$J=7 Hz, 3H); 1.55 ppm (s, 6H); 2.24 ppm (s, 3H); 2.82 ppm (s, 3H); 3.78 ppm (s, 3H); 4.50 ppm (q, $^3$J=7 Hz, 2H); 6.87 ppm (d, $^3$J=8 Hz, 1H); 6.92 ppm (s, 1H); 7.18 ppm (d, $^3$J=8 Hz, 1H); 7.54 ppm (d, $^3$J=8 Hz, 1H); 7.82 ppm (s, 1H); 7.97 ppm (d, $^3$J=8 Hz, 1H).

ESI Mass Spectrum: M$^+$=308.1 (100% relative intensity) [M+Na]=330.1 (20% relative intensity)

Example 1.18

5-Biphenyl-4-yl-1-ethyl-2,3,3-trimethyl-3H-indolium tetrafluoroborate

The synthesis proceeds according to variation 3 of the general synthesis procedure A), 407 mg of 5-(5,5-dimethyl-(1,3,2)dioxaborinane-2-yl)-2,3,3-trimethyl-3H-indole, and 455 mg of 4-bromo-biphenyl in 7.5 ml of 1,2-dimethoxythane, as well as 173 mg of tetrakis(triphenylphosphine) palladium(0) and 2.0 mL of potassium carbonate solution (2.76 g of potassium carbonate in 10 mL of water) being used. The resulting residue is purified chromatographically (silica gel, hexane/ethanol 9:1).

5-Biphenyl-4-yl-2,3,3-trimethyl-3H-indole is obtained in a yield of 264 mg (57% of the theoretical).

The 5-biphenyl-4-yl-2,3,3-trimethyl-3H-indole (264 mg), so obtained, is alkylated according to variation 3 of the general synthesis method C) with 1.3 mL of 1,2-dichloroethane and 1.02 mL of a triethyloxonium tetrafluoroborate solution (=1.90 g of triethyloxonium tetrafluoroborate in 10 mL of 1,2-dichloroethane). The product, so obtained, is washed with ethanol.

Yield: 220 mg (61% of the theoretical) 5-biphenyl-4-yl-1-ethyl-2,3,3-trimethyl-3H-indolium-tetrafluoroborate $^1$H-NMR (D$_6$DMSO): δ=1.47 ppm (t, $^3$J=7 Hz, 3H); 1.60 ppm (s, 6H); 2.84 ppm (s, 3H); 4.52 ppm (q, $^3$J=7 Hz, 2H); 7.40–7.52 ppm (m, 3H); 7.73–7.91 ppm (m, 6H); 8.00–8.06 ppm (m, 2H); 8.25 ppm (s, 1H).

ESI Mass Spectrum: M$^+$=340.3 (100% relative intensity) [M+Na]=362.1 (30% relative intensity)

Example 1.19

5-Benzo[b]thiophene-3-yl-1-ethyl-2,3,3-trimethyl-3H-indolium tetrafluoroborate

The synthesis proceeds according to variation 3 of the general synthesis procedure A), 407 mg of 5-(5,5-dimethyl-(1,3,2)dioxaborinane-2-yl)-2,3,3-trimethyl-3H-indole, and 416 mg of 3-bromothianaphthene in 7.5 ml of 1,2-dimethoxythane, as well as 173 mg of tetrakis(triphenylphosphine) palladium(0) and 2.0 mL of potassium carbonate solution (2.76 g of potassium carbonate in 10 mL of water) being used. The resulting residue is purified chromatographically (silica gel, hexane/ethanol 9:1).

5-benzo(b)thiophene-3-yl-2,3,3-trimethyl-3H-indole is obtained in a yield of 254 mg (58% of the theoretical).

The 5-benzo(b)thiophene-3-yl-2,3,3-trimethyl-3H-indole (254 mg), so obtained, is alkylated according to variation 3 of the general synthesis method C) with 1.3 mL of 1,2-dichloroethane and 1.05 mL of a triethyloxonium tetrafluoroborate solution (=1.90 g of triethyloxonium tetrafluoroborate in 10 mL of 1,2-dichloroethane). The product, so obtained, is washed with ethanol.

Yield: 180 mg (51% of the theoretical) 5-benzo[b]thiophene-3-yl-1-ethyl-2,3,3-trimethyl-3H-indolium tetrafluoroborate $^1$H-NMR (D$_6$DMSO): δ=1.48 ppm (t, $^3$J=7 Hz, 3H); 1.60 ppm (s, 6H); 2.85 ppm (s, 3H); 4.55 ppm (q, $^3$J=7 Hz, 2H); 7.43–7.55 ppm (m, 2H); 7.84–7.93 ppm (m, 2H); 7.98 ppm (s, 1H); 8.08–8.13 ppm (m, 3H).

ESI Mass Spectrum: M$^+$=320.1 (100% relative intensity) [M+Na]=342.1 (12% relative intensity)

Example 1.20

1-Ethyl-5-(1-ethyl-3-pyridiniumyl)-2,3,3-trimethyl-3H-indolium ditetrafluoroborate The synthesis proceeds according to variation 2 of the general synthesis procedure A), 0.77 g of 5-(5,5-dimethyl-(1,3,2)dioxaborinane-2-yl)-2,3,3-trimethyl-3H-indole and 0.38 g of 3-bromopyridine in 10 ml of 1,2-dimethoxythane, as well as 0.23 g of tetrakis(triphenylphosphine)palladium (0) and 0.66 g of potassium carbonate in 2.4 g of water being used. The resulting residue is adsorbed on silica gel and purified chromatographically (silica gel, hexane/acetone 6:4).

2,3,3-Trimethyl-5-(3 pyridinyl)-3H-indole is obtained in a yield of 0.36 g (77% of the theoretical).

The 2,3,3-trimethyl-5-(3 pyridinyl)-3H-indole (0.36 g), so obtained, is alkylated according to variation 3 of the general synthesis method C) with 0.64 g of triethyloxonium tetrafluoroborate in 5 mL of 1,2-dichloroethane. The product, so obtained, is washed with ethyl acetate and recrystallized from methanol.

Yield: 0.26 g (37% of the theoretical) 1-ethyl-5-(1-ethyl-3-pyridiniumyl)-2,3,3-trimethyl-3H-indolium ditetrafluoroborate $^1$H-NMR (D$_6$DMSO): δ=1.50 ppm (t, $^3$J=7 Hz, 3H); 1.50–1.75 ppm (m, 9H); 2.90 ppm (s, 3H); 4.57 ppm (q, $^3$J=7 Hz, 2H); 4.70 ppm (q, $^3$J=7 Hz, 2H); 8.18 ppm (d, $^3$J~8 Hz, 1H); 8.25 ppm (d, $^3$J~8 Hz, 1H); 8.32 ppm (~dd, $^3$J~8 Hz, 1H); 8.41 ppm (s, 1H); 9.02 ppm (d, $^3$J~8 Hz, 1H); 9.15 ppm (d, $^3$J~8 Hz, 1H); 9.55 ppm (s, 1H)

ESI Mass Spectrum: [M−1]$^+$=293.2 (100% relative intensity)

Example 1.21

1-Ethyl-5-furan-3-yl-2,3,3-trimethyl-3H-indolium tetrafluoroborate

The synthesis proceeds according to variation 2 of the general synthesis procedure A), 0.77 g of 5-(5,5-dimethyl-(1,3,2)dioxaborinane-2-yl)-2,3,3-trimethyl-3H-indole, and 0.50 g of 3-bromo-furan in 10 ml 1,2-dimethoxyethane, as well as 0.33 g of tetrakis(triphenylphosphine)palladium(0) and 0.94 g of potassium carbonate in 3.40 g of water being used. The resulting residue is adsorbed on silica gel and purified chromatographically (silica gel, hexane/acetone 8:2).

5-Furan-3-yl-2,3,3-trimethyl-3H-indole is obtained in a yield of 0.42 g (66% of the theoretical).

The 5-furan-3-yl-2,3,3-trimethyl-3H-indole (0.35 g), so obtained, is alkylated according to variation 3 of the general synthesis method C) with 0.35 g of triethyloxonium tetrafluoroborate in 5 mL of 1,2-dichloroethane. The product, so obtained, is washed with ethyl acetate.

Yield: 0.18 g (34% of the theoretical) 1-ethyl-5-furan-3-yl-2,3,3-trimethyl-3H-indolium tetrafluoroborate $^1$H-NMR (D$_6$DMSO): δ=1.45 ppm (t, $^3$J=7 Hz, 3H); 1.57 ppm (s, 6H); 2.82 ppm (s, 3H); 4.50 ppm (q, $^3$J=7 Hz, 2H); 7.11 ppm (s, 1H); 7.83 ppm (s, 1H); 7.90 ppm (d, $^3$J~9 Hz, 1H); 8.00 ppm (d, $^3$J~9 Hz, 1H); 8.15 ppm (s, 1H); 8.35 (s, 1H).

Example 1.22

1-Ethyl-2,3,3-trimethyl-5-(2-thienyl)-3H-indolium tetrafluoroborate

The synthesis proceeds according to variation 2 of the general synthesis procedure A), 0.77 g of 5-(5,5-dimethyl-(1,3,2)dioxaborinane-2-yl)-2,3,3-trimethyl- 3H-indole, and 0.56 g of 2-bromo-thiopene in 10 ml of 1,2-dimethoxythane, as well as 0.33 g of tetrakis(triphenylphosphine)palladium (0) and 0.94 g of potassium carbonate in 3.40 g of water being used. The resulting residue is adsorbed on silica gel and purified chromatographically (silica gel, hexane/acetone 8:2).

5-(Thiophene-2-yl)-2,3,3-trimethyl-3H-indole is obtained in a yield of 0.35 g (51% of the theoretical).

The 5-(thiophene-2-yl)2,3,3-trimethyl-3H-indole (0.32 g), so obtained, is alkylated according to variation 3 of the general synthesis method C) with 0.30 g of triethyloxonium tetrafluoroborate in 5 mL of 1,2-dichloroethane. The product, so obtained, is washed with ethyl acetate.

Yield: 0.31 g (65% of the theoretical) 1-ethyl-2,3,3-trimethyl-5-(2-thienyl)-3H-indolium tetrafluoroborate $^1$H-NMR (D$_6$DMSO): δ=1.46 ppm (t, $^3$J=7 Hz, 3H); 1.59 ppm (s, 6H); 2.83 ppm (s, 3H); 4.50 ppm (q, $^3$J=7 Hz, 2H); 7.22 ppm (m, 1H); 7.68 ppm (m, 2H); 7.90 ppm (d, $^3$J~8 Hz, 1H); 8.00 ppm (d, $^3$J~8 Hz, 1H); 8.19 ppm (s, 1H).

Examples 2.1 to 10.3

Hair Dyeing Agent

Component A1

| Compound of Formula (I)/(Ia) | Quantitative data in Tables 1–9 |
|---|---|
| cetyl stearyl alcohol | 12 g |
| lauryl ether sulfate, 28% aqueous solution | 10 g |
| ethanol | 23 g |
| water, fully desalinated | ad 100 g |

The cetyl stearyl alcohol is melted at 80° C. The lauryl ether sulfate is heated to 80° C. with 95% of the water and added to the molten cetyl stearyl alcohol and stirred until a cream results. The compound of Formula (I)/(Ia), mixed with the ethanol and the remainder of the water is added at room temperature. Optionally, the pH of the cream is adjusted with a 20% aqueous monoethanolamine solution to the values given in Tables 1 to 9.

Component A2

| Carbonyl compound/imine compound | Quantitative data in Tables 1–9 |
|---|---|
| cetyl stearyl alcohol | 12 g |
| lauryl ether sulfate, 28% aqueous solution | 10 g |
| ethanol | 23 g |
| water, fully desalinated | ad 100 g |

The cetyl stearyl alcohol is melted at 80° C. The lauryl ether sulfate is heated to 80° C. with 95% of the water and added to the molten cetyl stearyl alcohol and stirred until a cream results. The carbonyl/imine compound is added together with the ethanol and the remainder of the water at room temperature. Optionally, the pH of the cream is adjusted with a 20% aqueous monoethanolamine solution to the values given in Tables 1 to 9.

Component A1 and component A2 are mixed in the ratio of 1 to 1. the measured pH of the ready-for-use agent, so obtained, is referred to as pH$_m$ in Tables 1 to 9. The ready-for-use hair-dyeing agent, so obtained, is applied on the hair and distributed uniformly with a brush. After a period of action of 30 minutes at 40° C. the hair is washed with a shampoo, subsequently rinsed with lukewarm water and then dried.

At any convenient time (for example, after several days or weeks,) the hair can be decolorized completely once again within a period of 20 minutes at a temperature of 40° C. with an acidic (pH=5) sodium sulfite solution (component B).

The dyeing and decolorizing results are summarized in the following Tables 1 to 9.

The L*a*b* color values, given in the present examples, were determined with a Minolta, Type II Chromameter. The "L" value represents the brightness (that is, the lower the "L" value, the greater is the intensity of the color), whereas the "a" value is a measure of the red portion (the red portion varies with the value of "a"). The "b" value is a measure of the blue portion of the color (the more negative the value of "b", the greater is the blue portion).

Unless stated otherwise, all percentages in the present application are percentages by weight.

TABLE 1

Dyeing Results

| No. | Component A1); pH = 9.3<br>Component A2); pH = 4.5 | Shade after the coloring/ decolorization | Measured Color Values | L | a | b |
|---|---|---|---|---|---|---|
| 2.1 | A1) 5-(2,4-dimethoxyphenyl)-1,2,3,3-tetramethyl-3H-indole-1-ium tetrafluoroborate: 1.14 g | green-blue | Untreated hair:<br>After the coloring: | +83.30;<br>+44.16; | −0.48;<br>+20.20; | +10.40<br>−12.55 |
|  | A2) 3,5-dimethoxy-4-hydroxy-benzaldehyde: 0.52 g<br>pH$_m$ = 8.2 | after the decolorization | white |  |  |  |
| 2.2 | A1) 5-(2,4-dimethoxyphenyl)-1,2,3,3-tetramethyl-3H-indole-1-ium tetrafluoroborate: 1.14 g | red | Untreated hair:<br>After the coloring: | +83.30;<br>+51.64; | −0.48;<br>+35.83; | +10.40<br>0.00 |
|  | A2) 4-hydroxy-3-methoxy-benzaldehyde: 0.44 g<br>pH$_m$ = 8.1 | after the decolorization | white |  |  |  |

TABLE 1-continued

Dyeing Results

| No. | Component A1); pH = 9.3<br>Component A2); pH = 4.5 | Shade after the coloring/ decolorization | | Measured Color Values | | |
|---|---|---|---|---|---|---|
| | | | | L | a | b |
| 2.3 | A1) 5-(2,4-dimethoxyphenyl)-1,2,3,3-tetramethyl-3H-indole-1-ium tetrafluoroborate: 1.14 g<br>A2) 3-hydroxy-4-methoxy-benzaldehyde: 0.44 g<br>$pH_m$ = 8.5 | orange<br><br>after the decolorization | Untreated hair:<br>After the coloring:<br>white | +83.30;<br>+69.55; | −0.48;<br>+21.52; | +10.40<br>+36.57 |
| 2.4 | A1) 5-(2,4-dimethoxyphenyl)-1,2,3,3-tetramethyl-3H-indole-1-ium tetrafluoroborate: 1.14 g<br>A2) 3,4,5-trihydroxy-benzaldehyde: 0.50 g<br>$pH_m$ = 7.9 | green<br><br>after the decolorization | Untreated hair:<br>After the coloring:<br>white | +83.30;<br>+43.42; | −0.48;<br>+0.46; | +10.40<br>−7.12 |
| 2.5 | A1) 5-(2,4-dimethoxyphenyl)-1,2,3,3-tetramethyl-3H-indole-1-ium tetrafluoroborate: 1.14 g<br>A2) 4-(dimethylamino)benzaldehyde: 0.43 g<br>$pH_m$ = 8.6 | pink<br><br>after the decolorization | Untreated hair:<br>After the coloring:<br>pale pink | +83.30;<br>+66.20; | −0.48;<br>+25.17; | +10.40<br>−2.63 |

TABLE 2

Dyeing Results

| No. | Component A1); pH = 9.3<br>Component A2); pH = 4.5 | Shade after the coloring/ decolorization | | Measured Color Values | | |
|---|---|---|---|---|---|---|
| | | | | L | a | b |
| 3.1 | A1) 5-(1,3-benzodioxol-5-yl)-1,2,3,3-tetramethyl-3H-indole-1-ium tetrafluoroborate: 1.10 g<br>A2) 3,5-dimethoxy-4-hydroxy-benzaldehyde: 0.52 g<br>$pH_m$ = 7.8 | green-blue<br><br>after the decolorization | Untreated hair:<br>After the coloring:<br>white | +83.30;<br>+45.21; | −0.48;<br>+19.49; | +10.40<br>−13.48 |
| 3.2 | A1) 5-(1,3-benzodioxol-5-yl)-1,2,3,3-tetramethyl-3H-indole-1-ium tetrafluoroborate: 1.10 g<br>A2) 4-hydroxy-3-methoxy-benzaldehyde: 0.44 g<br>$pH_m$ = 7.8 | red<br><br>after the decolorization | Untreated hair:<br>After the coloring:<br>white | +83.30;<br>+50.63; | −0.48;<br>+35.31; | +10.40<br>−1.86 |
| 3.3 | A1) 5-(1,3-benzodioxol-5-yl)-1,2,3,3-tetramethyl-3H-indole-1-ium tetrafluoroborate: 1.10 g<br>A2) 3-hydroxy-4-methoxy-benzaldehyde: 0.44 g<br>$pH_m$ = 8.4 | orange<br><br>after the decolorization | Untreated hair:<br>After the coloring:<br>white | +83.30;<br>+69.73; | −0.48;<br>+21.11; | +10.40<br>+34.32 |
| 3.4 | A1) 5-(1,3-benzodioxol-5-yl)-1,2,3,3-tetramethyl-3H-indole-1-ium tetrafluoroborate: 1.10 g<br>A2) 3,4,5-trihydroxy-benzaldehyde: 0.50 g<br>$pH_m$ = 7.2 | green<br><br>after the decolorization | Untreated hair:<br>After the coloring:<br>pale green | +83.30;<br>+43.78; | −0.48;<br>−1.37; | +10.40<br>−8.67 |
| 3.5 | A1) 5-(1,3-benzodioxol-5-yl)-1,2,3,3-tetramethyl-3H-indole-1-ium tetrafluoroborate: 1.10 g<br>A2) 4-(dimethylamino)benzaldehyde: 0.43 g<br>$pH_m$ = 8.3 | pink<br><br>after the decolorization | Untreated hair:<br>After the coloring:<br>pale pink | +83.30;<br>+61.70; | −0.48;<br>+28.88; | +10.40<br>−6.46 |

TABLE 3

Dyeing Results

| No. | Component A1); pH = 8.3<br>Component A2); pH = 4.5 | Shade after the coloring/ decolorization | Measured Color Values | L | a | b |
|---|---|---|---|---|---|---|
| 4.1 | A1) 1,2,3,3-tetramethyl-5-(-2-trifluoromethyl)phenyl)-3H-indole-1-ium tetrafluoroborate: 1.17 g | violet | Untreated hair:<br>After the coloring: | +83.30;<br>+50.78; | −0.48;<br>+25.19; | +10.40<br>−8.79 |
|  | A2) 3,5-dimethoxy-4-hydroxy-benzaldehyde: 0.52 g<br>pH$_m$ = 7.3 | after the decolorization | white | | | |
| 4.2 | A1) 1,2,3,3-tetramethyl-5-(-2-trifluoromethyl)phenyl)-3H-indole-1-ium tetrafluoroborate: 1.17 g | red | Untreated hair:<br>After the coloring: | +83.30;<br>+58.54; | −0.48;<br>+38.06; | +10.40<br>+7.11 |
|  | A2) 4-hydroxy-3-methoxy-benzaldehyde: 0.44 g<br>pH$_m$ = 7.2 | after the decolorization | white | | | |
| 4.3 | A1) 1,2,3,3-tetramethyl-5-(-2-trifluoromethyl)phenyl)-3H-indole-1-ium tetrafluoroborate: 1.17 g | orange | Untreated hair:<br>After the coloring: | +83.30;<br>+77.82; | −0.48;<br>+12.45; | +10.40<br>+33.30 |
|  | A2) 3-hydroxy-4-methoxy-benzaldehyde: 0.44 g<br>pH$_m$ = 7.3 | after the decolorization | white | | | |
| 4.4 | A1) 1,2,3,3-tetramethyl-5-(-2-trifluoromethyl)phenyl)-3H-indole-1-ium tetrafluoroborate: 1.17 g | green | Untreated hair:<br>After the coloring: | +83.30;<br>+49.50; | −0.48;<br>+1.16; | +10.40<br>−5.41 |
|  | A2) 3,4,5-trihydroxy-benzaldehyde: 0.50 g<br>pH$_m$ = 7.1 | after the decolorization | pale yellow | | | |
| 4.5 | A1) 1,2,3,3-tetramethyl-5-(-2-trifluoromethyl)phenyl)-3H-indole-1-ium tetrafluoroborate: 1.17 g | pink | Untreated hair:<br>After the coloring: | +83.30;<br>+65.31; | −0.48;<br>+37.51; | +10.40<br>−2.58 |
|  | A2) 4-(dimethylamino) benzaldehyde: 0.43 g<br>pH$_m$ = 7.2 | after the decolorization | pale pink | | | |

TABLE 4

Dyeing Results

| No. | Component A1); pH = 7.7<br>Component A2); pH = 4.5 | Shade after the coloring/ decolorization | Measured Color Values | L | a | b |
|---|---|---|---|---|---|---|
| 5.1 | A1) 1,2,3,3-tetramethyl-5-(thiophene-3-yl)-3H-indolium iodide: 1.10 g | violet | Untreated hair:<br>After the coloring: | +83.30;<br>+28.95; | −0.48;<br>+31.75; | +10.40<br>−9.93 |
|  | A2) 3,5-dimethoxy-4-hydroxy-benzaldehyde: 0.52 g<br>pH$_m$ = 7.5 | after the decolorization | white | | | |
| 5.2 | A1) 1,2,3,3-tetramethyl-5-(thiophene-3-yl)-3H-indolium iodide: 1.10 g | red | Untreated hair:<br>After the coloring: | +83.30;<br>+40.66; | −0.48;<br>+46.78; | +10.40<br>+11.39 |
|  | A2) 4-hydroxy-3-methoxy-benzaldehyde: 0.44 g<br>pH$_m$ = 7.7 | after the decolorization | white | | | |
| 5.3 | A1) 1,2,3,3-tetramethyl-5-(thiophene-3-yl)-3H-indolium iodide: 1.10 g | orange | Untreated hair:<br>After the coloring: | +83.30;<br>+64.49; | −0.48;<br>+19.44; | +10.40<br>+56.13 |
|  | A2) 3-hydroxy-4-methoxy-benzaldehyde: 0.44 g<br>pH$_m$ = 7.6 | after the decolorization | white | | | |

TABLE 4-continued

Dyeing Results

| No. | Component A1); pH = 7.7<br>Component A2); pH = 4.5 | Shade after the coloring/<br>decolorization | Measured Color Values | L | a | b |
|-----|---|---|---|---|---|---|
| 5.4 | A1) 1,2,3,3-tetramethyl-5-(thiophene-3-yl)-3H-indolium iodide: 1.10 g<br>A2) 3,4,5-trihydroxy-benzaldehyde: 0.50 g<br>$pH_m$ = 7.5 | green<br><br>after the decolorization | Untreated hair:<br>After the coloring:<br>white | +83.30;<br>+32.98; | −0.48;<br>+9.90; | +10.40<br>−11.34 |
| 5.5 | A1) 1,2,3,3-tetramethyl-5-(thiophene-3-yl)-3H-indolium iodide: 1.10 g<br>A2) 4-(dimethylamino)benzaldehyde: 0.43 g<br>$pH_m$ = 7.5 | pink<br><br>after the decolorization | Untreated hair:<br>After the coloring:<br>white | +83.30;<br>+57.41; | −0.48;<br>+36.87; | +10.40<br>−8.02 |

TABLE 5

Dyeing Results

| No. | Component A1); pH = 3.6<br>Component A2); pH = 9.5 | Shade after the coloring/<br>decolorization | Measured Color Values | L | a | b |
|-----|---|---|---|---|---|---|
| 6.1 | A1) 5-phenyl-1,2,2,3-tetramethyl-1(3H)-indolium tetrafluoroborate: 3.88 g<br>A2) 3,5-dimethoxy-4-hydroxy-benzaldehyde: 2.10 g<br>$pH_m$ = 8.1 | blue<br><br>after the decolorization | Untreated hair:<br>After the coloring:<br>white | +83.30;<br>+28.29; | −0.48;<br>+33.60; | +10.40<br>−20.98 |
| 6.2 | A1) 5-phenyl-1,2,2,3-tetramethyl-1(3H)-indolium tetrafluoroborate: 3.88 g<br>A2) 4-hydroxy-3-methoxy-benzaldehyde: 1.75 g<br>$pH_m$ = 8.2 | red<br><br>after the decolorization | Untreated hair:<br>After the coloring:<br>white | +83.30;<br>+33.79; | −0.48;<br>+51.63; | +10.40<br>−4.12 |
| 6.3 | A1) 5-phenyl-1,2,2,3-tetramethyl-1(3H)-indolium tetrafluoroborate: 3.88 g<br>A2) 3-hydroxy-4-methoxy-benzaldehyde: 1.75 g<br>$pH_m$ = 8.9 | orange<br><br>after the decolorization | Untreated hair:<br>After the coloring:<br>white | +83.30;<br>+64.24; | −0.48;<br>+24.12; | +10.40<br>+47.90 |
| 6.4 | A1) 5-phenyl-1,2,2,3-tetramethyl-1(3H)-indolium tetrafluoroborate: 3.88 g<br>A2) 3,4-dihydroxy-benzaldehyde: 1.59 g<br>$pH_m$ = 8.3 | intensive claret<br><br>after the decolorization | Untreated hair:<br>After the coloring:<br>white | +83.30;<br>+24.68; | −0.48;<br>+22.92; | +10.40<br>−13.41 |
| 6.5 | A1) 5-phenyl-1,2,2,3-tetramethyl-1(3H)-indolium tetrafluoroborate: 3.88 g<br>A2) 4-(dimethylamino)benzaldehyde: 1.72 g<br>$pH_m$ = 8.9 | intensive pink<br><br>after the decolorization | Untreated hair:<br>After the coloring:<br>light pink | +83.30;<br>+42.56; | −0.48;<br>+55.06; | +10.40<br>−16.87 |

TABLE 6

Dyeing Results

| No. | Component A1); pH = 3.2<br>Component A2); pH = 9.5 | Shade after the coloring/ decolorization | | Measured Color Values | | |
| --- | --- | --- | --- | --- | --- | --- |
| | | | | L | a | b |
| 7.1 | A1) 1,2,3,3-tetramethyl-5-p-tolyl-3H-indolium tetrafluoroborate: 4.04 g<br>A2) 3,5-dimethoxy-4-hydroxy-benzaldehyde: 2.10 g<br>$pH_m$ = 7.6 | green<br>after the decolorization | white | Untreated hair:<br>After the coloring: | +83.30;<br>+35.40; | −0.48;<br>+25.32; | +10.40<br>−17.35 |
| 7.2 | A1) 1,2,3,3-tetramethyl-5-p-tolyl-3H-indolium tetrafluoroborate: 4.04 g<br>A2) 4-hydroxy-3-methoxy-benzaldehyde: 1.75 g<br>$pH_m$ = 7.1 | red<br>after the decolorization | white | Untreated hair:<br>After the coloring: | +83.30;<br>+42.05; | −0.48;<br>+43.01; | +10.40<br>−1.98 |
| 7.3 | A1) 1,2,3,3-tetramethyl-5-p-tolyl-3H-indolium tetrafluoroborate: 4.04 g<br>A2) 3-hydroxy-4-methoxy-benzaldehyde: 1.75 g<br>$pH_m$ = 8.4 | orange<br>after the decolorization | white | Untreated hair:<br>After the coloring: | +83.30;<br>+67.60; | −0.48;<br>+20.74; | +10.40<br>−37.67 |
| 7.4 | A1) 1,2,3,3-tetramethyl-5-p-tolyl-3H-indolium tetrafluoroborate: 4.04 g<br>A2) 3,4-dihydroxy-benzaldehyde: 1.59 g<br>$pH_m$ = 7.4 | claret<br>after the decolorization | light pink | Untreated hair:<br>After the coloring: | +83.30;<br>+33.64; | −0.48;<br>+19.55; | +10.40<br>−9.90 |
| 7.5 | A1) 1,2,3,3-tetramethyl-5-p-tolyl-3H-indolium tetrafluoroborate: 4.04 g<br>A2) 4-(dimethylamino) benzaldehyde: 1.72 g<br>$pH_m$ = 8.0 | intensive pink<br>after the decolorization | light pink | Untreated hair:<br>After the coloring: | +83.30;<br>+41.30; | −0.48;<br>+53.23; | +10.40<br>−19.57 |

TABLE 7

Dyeing Results

| No. | Component A1); pH = 3.2<br>Component A2); pH = 9.5 | Shade after the coloring/ decolorization | | Measured Color Values | | |
| --- | --- | --- | --- | --- | --- | --- |
| | | | | L | a | b |
| 8.1 | A1) 1,2,3,3-tetramethyl-5-naphthalene-1-yl-3H-indolium tetrafluoroborate: 2.23 g<br>A2) 3,5-dimethoxy-4-hydroxy-benzaldehyde: 2.10 g<br>$pH_m$ = 7.3 | blue<br>after the decolorization | white | Untreated hair:<br>After the coloring: | +83.30;<br>+36.90; | −0.48;<br>+29.93; | +10.40<br>−21.87 |
| 8.2 | A1) 1,2,3,3-tetramethyl-5-naphthalene-1-yl-3H-indolium tetrafluoroborate: 2.23 g<br>A2) 4-hydroxy-3-methoxy-benzaldehyde: 1.75 g<br>$pH_m$ = 7.1 | red<br>after the decolorization | white | Untreated hair:<br>After the coloring: | +83.30;<br>+46.06; | −0.48;<br>+42.94; | +10.40<br>−6.26 |
| 8.3 | A1) 1,2,3,3-tetramethyl-5-naphthalene-1-yl-3H-indolium tetrafluoroborate: 2.23 g<br>A2) 3,4-dihydroxy-benzaldehyde: 1.59 g<br>$pH_m$ = 7.4 | violet<br>after the decolorization | white | Untreated hair:<br>After the coloring: | +83.30;<br>+39.36; | −0.48;<br>+15.86; | +10.40<br>−12.47 |
| 8.4 | A1) 1,2,3,3-tetramethyl-5-naphthalene-1-yl-3H-indolium tetrafluoroborate: 2.23 g<br>A2) 4-(dimethylamino)-benzaldehyde: 1.72 g<br>$pH_m$ = 8.3 | pink<br>after the decolorization | white | Untreated hair:<br>After the coloring: | +83.30;<br>+51.44; | −0.48;<br>+44.31; | +10.40<br>−16.38 |

TABLE 8

Dyeing Results

| No. | Component A1); pH = 4.0<br>Component A2); pH = 9.5 | Shade after the coloring/ decolorization | | Measured Color Values | | |
|---|---|---|---|---|---|---|
| | | | | L | a | b |
| 9.1 | A1) 1-ethyl-2,3,3-trimethyl-5-(4-methylsulfanyl-phenyl)-3H-indolium tetrafluoroborate: 2.28 g | green blue | Untreated hair:<br>After the coloring: | 63.30;<br>47.81; | −0.48;<br>+15.05; | +10.40<br>−12.33 |
| | A2) syringealdehyde: 1.05 g<br>pH$_m$ = 8.0 | after the decolorization | yellow | | | |
| 9.2 | A1) 1'-acetyl-1-ethyl-2,3,3-trimethyl-2',3'-dihydro-3H-1'H-[5,5']biindolyl-1-ium tetrafluoroborate: 2.50 g | blue | Untreated hair:<br>After the coloring: | 63.30;<br>32.60; | −0.48;<br>+14.44; | +10.40<br>−17.04 |
| | A2) syringealdehyde: 1.05 g<br>pH$_m$ = 7.9 | after the decolorization | yellow | | | |
| 9.3 | A1) 1-ethyl-2,3,3-trimethyl-5-naphthalene-2-yl-3H-indolium tetrafluoroborate: 2.31 g | green | Untreated hair:<br>After the coloring: | 63.30;<br>54.74; | −0.48;<br>+8.51; | +10.40<br>−5.53 |
| | A2) syringealdehyde: 1.05 g<br>pH$_m$ = 7.7 | after the decolorization | yellow | | | |
| 9.4 | A1) 1-ethyl-5-(6-hydroxy-naphthalene-2-yl)-2,3,3-trimethyl-3H-indolium tetrafluoroborate: 2.40 g | green | Untreated hair:<br>After the coloring: | 63.30;<br>58.78; | −0.48;<br>+3.75; | +10.40<br>−0.52 |
| | A2) syringealdehyde: 1.05 g<br>pH$_m$ = 7.2 | after the decolorization | yellow | | | |
| 9.5 | A1) 5-anthracene-9-yl-1-ethyl-2,3,3-trimethyl-3H-indolium tetrafluoroborate: 2.60 g | green | Untreated hair:<br>After the coloring: | 63.30;<br>56.27; | −0.48;<br>+13.39; | +10.40<br>−6.08 |
| | A2) syringealdehyde: 1.05 g<br>pH$_m$ = 7.6 | after the decolorization | light yellow | | | |
| 9.6 | A1) 5-(3,5-dimethyl-phenyl)-1-ethyl-2,3,3-trimethyl-3H-indolium tetrafluoroborate: 2.18 g | blue | Untreated hair:<br>After the coloring: | 63.30;<br>45.89; | −0.48;<br>+18.46; | +10.40<br>−17.00 |
| | A2) syringealdehyde: 1.05 g<br>pH$_m$ = 7.8 | after the decolorization | white | | | |
| 9.7 | A1) 1-ethyl-5-(4-methoxy-2-methyl-phenyl)-2,3,3-trimethyl-3H-indolium tetrafluoroborate: 2.27 g | blue | Untreated hair:<br>After the coloring: | 63.30;<br>40.85; | −0.48;<br>+26.18; | +10.40<br>−17.64 |
| | A2) syringealdehyde: 1.05 g<br>pH$_m$ = 8.2 | after the decolorization | yellow | | | |
| 9.8 | A1) 5-benzo[b]thiophene-3-yl-1-ethyl-2,3,3-trimethyl-3H-indolium tetrafluoroborate: 2.34 g | bluegreen | Untreated hair:<br>After the coloring: | 63.30;<br>48.66; | −0.48;<br>+16.20; | +10.40<br>−14.90 |
| | A2) syringealdehyde: 1.05 g<br>pH$_m$ = 8.0 | after the decolorization | yellow | | | |

TABLE 9

Dyeing Results

| No. | Component A1); pH = 4.1<br>Component A2); pH = 9.4 | Shade after the coloring/ decolorization | | Measured Color Values | | |
|---|---|---|---|---|---|---|
| | | | | L | a | b |
| 10.1 | A1) 1-ethyl-5-(1-ethyl-3-pyridiniumyl)-2,3,3-trimethyl-3H-indolium ditetrafluoroborate: 2.43 g | green blue | Untreated hair:<br>After the coloring: | 82.17;<br>33.68; | +0.55;<br>+22.38; | +11.38<br>−6.94 |
| | A2) syringealdehyde: 1.05 g<br>pH$_m$ = 8.0 | after the decolorization | yellow | | | |
| 10.2 | A1) 1-ethyl-5-furan-3-yl-2,3,3-trimethyl-3H-indolium-tetrafluoroborate: 2.34 g | green blue | Untreated hair:<br>After the coloring: | 82.17;<br>39.69; | +0.55;<br>+22.66; | +11.38<br>−17.58 |
| | A2) syringealdehyde: 1.05 g<br>pH$_m$ = 7.6 | after the decolorization | white | | | |

TABLE 9-continued

Dyeing Results

| No. | Component A1); pH = 4.1<br>Component A2); pH = 9.4 | Shade after the coloring/ decolorization | Measured Color Values | | |
|---|---|---|---|---|---|
| | | | L | a | b |
| 10.3 | A1) 1-ethyl-2,3,3-trimethyl-5-(2-thienyl)-3H-indolium tetrafluoroborate: 2.05 g<br>A2) syringealdehyde: 1.05 g<br>$pH_m$ = 7.5 | blue<br><br>after the decolorization | Untreated hair:<br>After the coloring:<br><br>white | 82.17;<br>40.05; | +0.55;<br>+19.91; | +11.38<br>−22.64 |

What is claimed is:

1. An agent for dyeing keratin fibers (A), which is prepared by mixing two components (A1) and (A2), wherein component (A1) contains at least one compound of Formula (I) and/or (Ia)

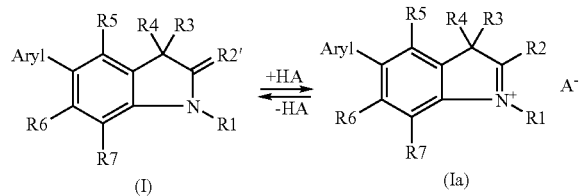

in which

R1 is a linear or branched C1–C8 alkyl group, a C1 to C8 monohydroxyalkyl group, a C2–C8 polyhydroxyalkyl group, a C1–C8 alkoxy-(C1–C8) alkyl group, a thio-(C1–C8)-alkyl group, a —(CH$^2$)$_m$—X—(CH$_2$)$_n$—Y—(CH$_2$)$_p$R$^a$ group, a —(CH$_2$)$_n$—X—R$^a$ group, a —(CH$^2$)$_m$—Y—(CH$_2$)$_n$—X—(CH$_2$)$_p$—R$^a$ group, a —(CH$^2$)$_m$—CO—(CH$_2$)$_p$—X—R$^a$ group, a —(CH$^2$)$_p$—R$^a$ group, a —(CH$^2$)$_m$—X—(CH$_2$)$_p$—CO—Y—R$^a$ group or one of the 3 following groups

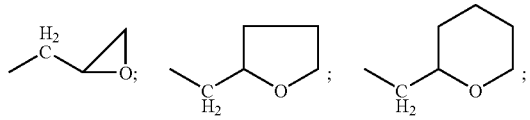

in which X and Y, independently of one another, are an oxygen atom, a sulfur atom or an NR$^b$ group, R$^a$ and R$^b$, independently of one another, are a hydrogen atom, an optionally substituted aromatic carbon ring or heterocyclic ring or a linear or branched C1–C8 alkyl group, m and n, independently of one another are a whole number from 1 to 6 and p is a whole number from 0 to 6, R2 is a linear C1–C6 alkyl group, R2' is a CH—R' group, in which R' is hydrogen or a C1–C5 alkyl group, R3 and R4 independently of one another are a linear or branched C1–C4 alkyl group, a —(CH$_2$)$_n$—R$^c$ group, a —(CH$_2$)$_m$—CHR$^c$—X—(CH$_2$)$_n$—R$^c$ group, a —(CH$^2$)$_n$—CO—R$^c$ group, a —(CH$_2$)$_n$—CO—XR$^c$ group, a —(CH$_2$)$_n$—CN group, a —(CH$_2$)$_n$—CH=C(CH$_3$)$_2$ group, a —(CH$_2$)$_m$—X—CHR$^c$—(CH$_2$)$_n$—R$^c$ group or a —(CH$_2$)$_n$CH=CH group, X being an oxygen atom, a sulfur atom or an NR$^b$ group, m and n, independently of one another, are a whole number from 1 to 6 and R$^c$ is a hydrogen atom, an optionally substituted aromatic carbocyclic ring or heterocyclic ring or a linear or branched C1–C6 alkyl group, with the proviso that R3 and R4 linked by a (CH$_2$)$_n$ group, with n a whole number from 1 to 3, can form a spiro compound together with the 3H carbon atom, R5, R6 and R7, independently of one another, are a hydrogen atom, a linear or branched C1–C4 alkyl group, a C1–C4 hydroxyalkyl group, a hydroxy group, a methoxy group, a benzyl group, a halogen atom, a nitro group, a nitroso group, a cyano group, a trifluoromethyl group, a —CHO group, a —COR$^d$ group, a —COOH group, a —CO$_2$R$^d$ group, an —OCOR$^d$ group, an —OCH$_2$aryl group, an —SO$_2$NH$_2$ group, an —NH$_2$ group, an —NH$_3^+$ group, an —NHR$^d$ group, an —NH$_2$R$^{d+}$ group, an —N(R$^d$)$_2$ group, an —N(R$^d$)$_3^+$ group, an —NHCOR$^d$ group, an —NHCOOR$^d$ group, a —CH$_2$NH$_2$ group, a —CH$_2$NHR$^d$ group, a —CH$_2$N(R$^d$)$_2$ group, a —CO$_2$CF$_3$ group, a —PO(OR$^d$)$_2$ group, an —SO$_2$CHF$_2$ group, an —SO$_2$CF$_3$ group, an —SO$^2$R$^d$ group or an —SR$^d$ group, R$^d$ being a hydrogen atom, an optionally substituted aromatic carbocyclic or heterocyclic ring or a C1–C6 alkyl group, with the proviso that R6 and R7, jointly with adjacent carbon atoms of the aromatic nucleus, can also form a 5- or 6-membered alicyclic or aromatic ring, which optionally may contain one or more carbon, nitrogen and/or oxygen atoms, and aryl is a substituted pyrimidyl group, a cyclic group of Formula (IX) or a heterocyclic group of Formula (X) or (XI) or (XII)

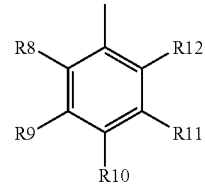

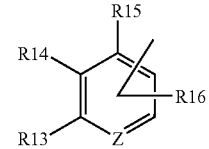

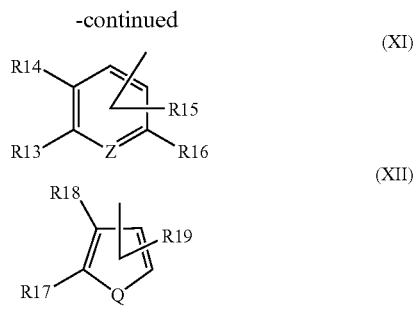

in which R8, R9, R10, R11, R12, R13, R14, R15, R16, R17, R18 and R19 independently of one another are a hydrogen atom, a linear or branched C1–C4 alkyl group, a C1–C4 hydroxyalkyl group, a hydroxy group, a methoxy group, a benzyl group, a halogen atom, a nitro group, a nitroso group, a cyano group, a trifluoromethyl group, a —CHO group, a —COR$^e$ group, a —COOH group, a —CO$_2$R$^e$ group, an —OCOR$^e$ group, an —OCH$_2$ aryl group, an —SO$_2$NH$_2$ group, an —NH$_2$ group, an —(NH$_3$)$^+$ group, an —NHR$^e$ group, an —(NH$_2$R$^e$)$^+$ group, an —N(R$^e$)$_2$ group, an —(N(R$^e$)$_3$)$^+$ group, an —NHCOR$^e$ group, an —NH-COOR$^e$ group, a —CH$_2$NH$_2$ group, a —CH$_2$NHR$^e$ group, a —CH$_2$N(R$^e$)$_2$ group, a —CO$_2$CF$_3$ group, a —PO(OR$^e$)$_2$ group, an —SO$_2$CHF$_2$ group, an —SO$_2$CF$_3$ group, an —SO$_2$R$^e$ group or an —SR$^e$ group, with R$^e$ a hydrogen atom, an optionally substituted aromatic carbocyclic or heterocyclic ring or a C1–C6 alkyl group, with the proviso that two adjacent R8 to R19 groups, jointly with the carbon atoms of the aromatic ring, can also form a 5- or 6-membered alicyclic or aromatic nucleus, which optionally may contain one or more sulfur, nitrogen and/or oxygen atoms, and Z is sulfur, nitrogen, oxygen or an N$^{(+)}$—R$^f$ group,
Q is sulfur, nitrogen, oxygen or an N—R$^f$ group,
R$^f$ is hydrogen, a C$_1$–C$_6$ alkyl group, a C2–C4 hydroxyalkyl group, a phenyl group, an acetyl group or sulfonyl group,
A$^-$ is an anion of an organic or inorganic acid, and component (A2) contains at least one carbonyl compound and/or imine compound.

2. The agent of claim 1, wherein said at least one compound of Formula (I) and/or (Ia) is selected from the group consisting of 5-(2,4-dimethoxyphenyl)-1,3,3-trimethyl-2-methylene-indoline, 5-(1,3-benzodioxol-5-yl)-1,3,3-trimethyl-2-methylene-indoline, 5-(2-(trifluoromethyl)phenyl)-1,3,3-trimethyl-2-methylene-indoline, 5-(phenyl)-1,3,3-trimethyl-2-methylene-indoline, 5-(p-tolyl)-1,3,3-trimethyl-2-methylene-indoline, 5-(naphthalene-1-yl)-1,3,3-trimethyl-2-methylene-indoline, 5-(4-methylsulfanyl-phenyl)-1,3,3-trimethyl-2-methylene-indoline, 5-(4-hydroxy-phenyl)-1,3,3-trimethyl-2-methylene-indoline, 5-(naphthalene-2-yl)-1,3,3-trimethyl-2-methylene-indoline, 5-(2-hydroxy-naphthalene-6-yl)-1,3,3-trimethyl-2-methylene-indoline, 5-(anthracene-9-yl)-1,3,3-trimethyl-2-methylene-indoline, 5-(3,5-dimethyl-phenyl)-1,3,3-trimethyl-2-methylene-indoline, 5-(acenaphthene-5-yl)-1,3,3-trimethyl-2-methylene-indoline, 5-(4-methoxy-2-methyl-phenyl)-1,3,3-trimethyl-2-methylene-indoline, 5-(biphenyl-4-yl)-1,3,3-trimethyl-2-methylene-indoline, 5-(benzo[b]thiophene-3-yl)-1-ethyl-1,3,3-dimethyl-2-methylene-indoline, 1-ethyl-3-(1ethyl-3,3-dimethyl-2-methylene-2,3-dihydro-1H-indole-5-yl)pyridinium tetrafluoroborate, 5-(furan-3-yl)-1-ethyl-3,3-dimethyl-2-methylene-indoline, 5-(thiophene-3-yl)-1,3,3-trimethyl-2-methylene-indoline, 5-(thiophene-2-yl)-1-ethyl-3,3-dimethyl-2-methylene-indoline and 1-(1',3',3'-trimethyl-2'-methylene-2,3,2',3'-tetrahydro-1'H-[5,5']biindolyl-1-yl)-ethanone, or is a salt thereof.

3. The agent of claim 1, wherein said at least one carbonyl compound and/or imine compound is selected from the group consisting of 4-hydroxy-3-methoxy-benzaldehyde, 3-hydroxy-4-methoxy-benzaldehyde, 3,4-dihydroxy-benzaldehyde, 4-hydroxy-benzaldehyde, 3,5-dimethoxy-4-hydroxy-benzaldehyde, 4-dimethylaminobenzaldehyde, 4-methyl-5-imidazole-carboxaldehyde, 4-dimethylamino-cinnamon-aldehyde, 4-hydroxy-2-methoxy-benzaldehyde, 3,5-dimethyl-4-hydroxybenzaldehyde, 4-dimethylamino-2-methoxy-benzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxy-biphenyl-1-carbaldehyde, 2-hydroxy-3-methoxybenzaldehyde, 2,4-dihydroxy-benzaldehyde, 3,4-dihydroxy-benzaldehyde, 2,5-dihydroxy-benzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxy-benzaldehyde, 2,5-dimethoxybenzaldehyde; 3,5-dimethoxybenzaldehyde; 3,4-dimethoxybenzaldehyde; indole-3-carbaldehyde; benzene-1,4-dicarbaldehyde; 4-ethoxybenzaldehyde; 2-methyl-1,4-naphthraquinone; 4-carboxybenzaldehyde; 4-hydroxy-3-methoxycinnamaldehyde; 3,5-dimethoxy-4-hydroxycinnamaldehyde; 3-methoxy-4-(1-pyrrolidinyl)benzaldehyde; 4-diethylamino-3-methoxy-benzaldehyde; 1,2-phthalic dialdehyde; pyrrole-2-aldehyde; thiophene-2-aldehyde; thiophene-3-aldehyde; chromone-3-carboxaldehyde; 6-methyl-4-keto-1(4H)-benzopyran-3-carbaldehyde; N-methylpyrrole-2-aldehyde; 5-methylfurfural; 6-hydroxychromene-3-carboxaldehyde; 6-methylindole-3-carboxaldehyde; 4-dibutylamino-benzaldehyde; N-ethylcarbazole-3-aldehyde; 4-diethylamino-2-hydroxy-benzaldehyde; 3,4-dimethoxy-5-hydroxybenzaldehyde; 5-[4-(diethylamino)phenyl]-2,4-pentadienal; 2,3-thiophene dicarboxaldehyde; 2,5-thiophene dicarboxaldehyde; 2-methoxy-1-naphthaldehyde; 3-ethoxy-4-hydroxybenzaldehyde; 2-nitrobenzaldehyde; 3-nitrobenzaldehyde; 4-nitrobenzaldehyde; 4-{[(2-hydroxyethyl)imino]methyl}-2-methoxyphenol; 5-{[(2-hydroxyethyl)imino]methyl}-2-methoxyphenol; 2,6-dimethoxy-4-{[(2-hydroxyethyl)imino]methyl}phenol; 4-{[(2-hydroxyethyl)imino]methyl}-phenol; 1,2-dihydroxy-4-{[(2-hydroxyethyl)imino]methyl}benzene; N,N-dimethyl-4-{[(2-hydroxyethyl)imino]methyl}aniline; 1,2-dihydroxy-3-{[(2-hydroxyethyl)-imino]methyl}benzene; 4-{[(3-hydroxypropyl)imino]methyl}phenol; 2,6-dimethoxy-4-{[(3-hydroxypropyl)imino]-methyl}phenol; 4-{[(2,3-dihydroxypropyl)imino]-methyl}phenol; 2,6-dimethoxy-4-{[(2,3-dihydroxypropyl)imino]methyl}phenol; 2-[(4-hydroxybenzylidene)-amino]-propane-1,3-diol, 2-[(4hydroxy-3,5-dimethoxy-benzylidene)amino]propane-1,3-diol; 4-{[(2-hydroxy-2-phenylethyl)-imino]-methyl}phenol; 2,6-dimethoxy-4-{[(1-phenyl-2-hydroxyethyl)imino]-methyl}phenol; 4-{[(2-hydroxyphenyl)imino]methyl}-phenol; 2,6-dimethoxy-4-{[(2-hydroxyphenyl)-imino]methyl}phenol; 5-guanidino-2-[(4-hydroxybenzylidene)amino]pentanoic acid; 2-[(4-dimethylaminonaphthalen-1-yl-methylene)amino]ethanol; 5-guanidino-2-[(4-hydroxy-3,5-dimethoxybenzylidene)-amino]pentanoic acid; 2-[(4-hydroxy-3,5-dimethoxybenzylidene)-amino]-3-(3H-imidazole-4-yl)-propionic acid, 2-[(4-hydroxy-benzylidene)-amino]-3-(3H-imidazole-4-yl)- propionic acid, 2-[(4-hydroxy-3,5-dimethoxy-benzylidene)-amino]-3-(1H-indole-3-yl)-propionic acid, 2-[(4-hydroxy-benzylidene)-amino]-3-(1H-indole-3-yl)-propionic acid, 2-(((2-hydroxyethyl)-imino)methyl)phenol, 1,2-dihydroxy-3-(((2-hydroxyethyl)imino)methyl)benzene, 1,2,3-trihydroxy-4-(((2-hydroxyethyl)-imino)-methyl)benzene, 1,2,3,4-tetrahydroxy-5-(((2-hydroxyethyl)imino)methyl)-benzene and 1,2,4-trihydroxy-4-(((2-hydroxy-ethyl)imino)methyl)benzene.

4. The agent of claim 1, having a pH of 3 to 11.

5. The agent of claim 1, wherein said at least one compound of Formula (I) and/or (Ia) is contained in the component (A1) in a total amount of 0.02 to 20 percent by weight and said at least one carbonyl compound and/or imine compound is contained in the component (A2) in a total amount of 0.02 to 20 percent by weight.

6. The agent of claim 1, wherein said at least one compound of Formula (I) and/or (Ia) is contained in the agent in a total amount of 0.01 to 10 percent by weight and said at least one carbonyl compound and/or imine compound is contained in the agent in a total amount of 0.01 to 10 percent by weight.

7. The agent of claim 1, in the form of a solution, an emulsion, a foam, a cream or a gel.

8. The agent of claim 1, wherein the component (A1) and/or the component (A2) additionally contain at least one substantive dye and said at least one substantive dye is selected from the group consisting of acidic dyes, basic dyes, nitro dyes, azo dyes quinone dyes and triphenylmethane dyes.

9. A method for temporarily dyeing keratin fibers, in which the keratin fibers are dyed with an agent of claim 1 and then at any later, convenient time the dyed keratin fibers are decolorized by means of a decolorizing agent, which comprises a sulfite-containing preparation.

10. The method of claim 9, wherein the decolorizing agent is allowed to act for 5 to 60 minutes at a temperature of 20° to 50° C. on the keratin fibers.

11. A compound of Formula (I) or (Ia),

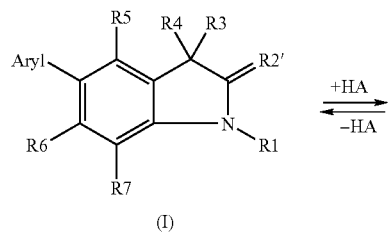

(I)

(Ia)

in which
R1 is a linear or branched C1–C8 alkyl group, a C1 to C8 monohydroxyalkyl group, a C2–C8 polyhydroxyalkyl group, a C1–C8 alkoxy-(C1–C8) alkyl group, a thio-(C1–C8)-alkyl group, a —(CH$^2$)$_m$—X—(CH$_2$)$_n$—Y—(CH$_2$)$_n$R$^a$ group, a —(CH$_2$)$_n$—X—R$^a$ group, a —(CH$_2$)$_m$—Y—(CH$_2$)$_n$—X—(CH$_2$)$_p$—R$^a$ group, a —(CH$^2$)$_m$—CO—(CH$_2$)$_p$—X—R$^a$ group, a —(CH$_2$)$_p$—R$^a$ group,
a —(CH$_2$)$_m$—X—(CH2)$_p$-CO—Y—R$^a$ group or one of the 3 following groups

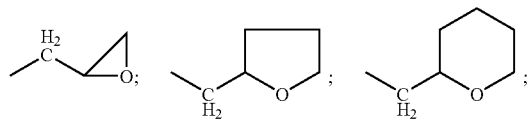

in which X and Y, independently of one another, are an oxygen atom, a sulfur atom or an NR$^b$ group, R$^a$ and R$^b$, independently of one another, are a hydrogen atom, an optionally substituted aromatic carbon ring or a heterocyclic ring or a linear or branched C1–C8 alkyl group, m and n, independently of one another are a whole number from 1 to 6 and p is a whole number from 0 to 6, R2 is a linear C1–C6 alkyl group, R2' is a CH—R' group, in which R' is hydrogen or a C1–C5 alkyl group, R3 and R4 independently of one another are a linear or branched C1–C4 alkyl group, a —(CH$_2$)$_n$—R$^c$ group, a —(CH$_2$)$_m$—CHR$^c$—X—(CH$_2$)$_n$—R$^c$ group, a —(CH$_2$)$_n$—CO—R$^c$ group, a —(CH$_2$)$_n$—CO—XR$^c$ group, a —(CH$_2$)$_n$—CN group, a —(CH$_2$)$_n$—CH═C(CH$_3$)$_2$ group, a —(CH$_2$)$_m$—X—CHR$^c$—(CH$_2$)$_n$—R$^c$ group or a —(CH$_2$)$_n$CH═CH group, and X being an oxygen atom, a sulfur atom or an NR$^b$ group, m and n, independently of one another, are a whole number from 1 to 6 and R$^c$ is a hydrogen atom, an optionally substituted aromatic carbocyclic ring or heterocyclic ring or a linear or branched C1–C6 alkyl group, with the proviso that R3 and R4 linked by a (CH$_2$)$_n$ group, with n being a whole number from 1 to 3, can also form a spiro compound together with the 3H Carbon atom, R5, R6 and R7, independently of one another, are a hydrogen atom, a linear or branched C1–C4 alkyl group, a C1–C4 hydroxyalkyl group, a hydroxy group, a methoxy group, a benzyl group, a halogen atom, a nitro group, a nitroso group, a cyano group, a trifluoromemyl group, a —CHO group, a —COR$^d$ group, a —COOH group, a —CO$_2$R$^d$ group, an —OCOR$^d$ group, an —OCH$_2$aryl group, an —SO$_2$NH$_2$ group, an —NH$_2$ group, an —NH$_3^+$ group, an —NHR$^d$ group, an —NH$_2$R$^{d+}$ group, an —N(R$^d$)$_2$ group, an —N(R$^d$)$_3^+$ group, an —NHCOR$^d$ group, an —NHCOOR$^d$ group, a —CH$_2$NH$_2$ group, a —CH$_2$NHR$^d$ group, a —CH$_2$N(R$^d$)$_2$ group, a —CO$_2$CF$_3$ group, a —PO(OR$^d$)$_2$ group, an —SO$_2$CHF$_2$ group, an —SO$_2$CF$_3$ group, an —SO$^2$R$^d$ group or an —SR$^d$ group, R$^d$ being a hydrogen atom, an optionally substituted aromatic carbocyclic or heterocyclic ring or a C1–C6 alkyl group, with the proviso that R6 and R7 groups, jointly with adjacent carbon atoms of the aromatic nucleus, can also form a 5- or 6-membered alicyclic or aromatic ring, which optionally may contain one or more sulfur, nitrogen and/or oxygen atoms, and aryl is a substituted pyrimidyl group, a cyclic group of Formula (IX) or a heterocyclic group of Formula (X) or (XI) or (XII)

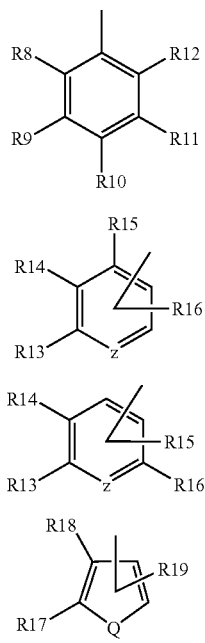

(IX)

(X)

(XI)

(XII)

in which R8, R9, R10, R11, R12, R13, R14, R15, R16, R17, R18 and R19 independently of one another are a hydrogen atom, a linear or branched C1–C4 alkyl group, a C1–C4 hydroxyalkyl group, a hydroxy group, a methoxy group, a benzyl group, a halogen atom, a nitro group, a nitroso group, a cyano group, a trifluoromethyl group, a —CHO group, a —COR$^e$ group, a —COOH group, a —CO$_2$R$^e$ group, an —OCOR$^6$ group, an —OCH$_2$aryl group, an —SO$_2$NH$_2$ group, an —NH$_2$ group, an —(NH$_3$)$^+$ group, an —NHR$^e$ group, an —(NH$_2$R$^e$)$^+$ group, an —N(R$^e$)$_2$ group, an —(N(R$^e$)$_3$)$^+$ group, an —NHCOR$^e$ group, an —NHCOOR$^e$ group, a —CH$_2$NH$_2$ group, a —CH$_2$NHR$^e$ group, a —CH$_2$N(R$^e$)$_2$ group, a —CO$_2$CF$_3$ group, a —PO(OR$^e$)$_2$ group, an —SO$_2$CHF$_2$ group, an —SO$_2$CF$_3$ group, an —SO$_2$R$^e$ group or an —SR$^e$ group, with R$^e$ a hydrogen atom, an optionally substituted aromatic carbocyclic or heterocyclic ring or a C1–C6 alkyl group, with the proviso that two adjacent R8 to R19 groups, jointly with the carbon atoms of the aromatic nucleus, can also form a 5- or 6-membered alicyclic or aromatic ring of the aromatic nucleus, which optionally may contain one or more sulfur, nitrogen and/or oxygen atoms, and Z is sulfur, nitrogen, oxygen or an N$^+$—R$^f$ group, Q is sulfur, nitrogen, oxygen or an N—R$^f$ group, R$^f$ is hydrogen, a C$_1$–C$_6$ alkyl group, a C2–C4 hydroxyalkyl group, a phenyl group, an acetyl group or sulfonyl group, A$^-$ is an anion of an organic or inorganic acid, with the proviso that, when R10 is hydrogen or a methoxy group, R2' or R2 is a methylene or methyl group and, when the R1, R3 and R4 groups simultaneously represent a methyl group, at least one of the R5 to R12 groups is different from hydrogen; and with the proviso that, when R1 is an ethyl group, R2 to R4 each represent a methyl group and Aryl represents the cyclic group of formula IX, then at least one of R5 to R12 is different from hydrogen.

* * * * *